(12) United States Patent
Ishihara et al.

(10) Patent No.: US 8,060,172 B2
(45) Date of Patent: Nov. 15, 2011

(54) IN-VIVO INFORMATION MEASUREMENT APPARATUS

(75) Inventors: Yasushige Ishihara, Tokyo (JP); Naoki Miura, Tokyo (JP); Hironobu Takizawa, Tokyo (JP); Tianyu Xie, Tokyo (JP)

(73) Assignee: Olympus Corporation, Tokyo (JP)

( * ) Notice: Subject to any disclaimer, the term of this patent is extended or adjusted under 35 U.S.C. 154(b) by 1485 days.

(21) Appl. No.: 11/086,152

(22) Filed: Mar. 22, 2005

(65) Prior Publication Data

US 2005/0267340 A1 Dec. 1, 2005

(30) Foreign Application Priority Data

Mar. 29, 2004 (JP) ................................ 2004-096497
May 19, 2004 (JP) ................................ 2004-149513

(51) Int. Cl.
*A61B 5/05* (2006.01)
*A61B 1/06* (2006.01)
(52) U.S. Cl. ........................................ 600/342; 600/343
(58) Field of Classification Search ................ 600/132, 600/160, 178, 310, 407, 437, 459–467, 101, 600/170, 182, 317, 323–329, 342–343, 473–478; 606/13–17; 128/916, 899

See application file for complete search history.

(56) References Cited

U.S. PATENT DOCUMENTS

| | | | | |
|---|---|---|---|---|
| 4,223,680 A | * | 9/1980 | Jobsis | 600/324 |
| 4,281,645 A | * | 8/1981 | Jobsis | 600/324 |
| 4,972,331 A | * | 11/1990 | Chance | 600/310 |
| 5,187,672 A | * | 2/1993 | Chance et al. | 600/407 |
| 5,290,275 A | * | 3/1994 | Kittrell et al. | 606/15 |
| 5,596,986 A | * | 1/1997 | Goldfarb | 600/323 |
| 5,692,504 A | | 12/1997 | Essenpreis et al. | |
| 5,779,631 A | * | 7/1998 | Chance | 600/328 |
| 5,800,343 A | * | 9/1998 | Takeuchi et al. | 600/132 |
| 6,055,451 A | * | 4/2000 | Bambot et al. | 600/476 |
| 6,070,096 A | * | 5/2000 | Hayashi | 600/477 |

(Continued)

FOREIGN PATENT DOCUMENTS

JP 05-103774 4/1993

(Continued)

OTHER PUBLICATIONS

Japanese Office Action dated Jun. 8, 2010.

*Primary Examiner* — Francis Jaworski
(74) *Attorney, Agent, or Firm* — Scully, Scott, Murphy & Presser, P.C.

(57) ABSTRACT

An in-vivo information measurement apparatus having an insertion part; a light projection unit, provided at a tip of the insertion part, irradiates an examination site with intensity-modulated light which is intensity modulated at a first frequency; a light receiving unit receives return light from the examination site; an optical detector detects return light; an in-vivo information calculation unit calculates in-vivo information for the examination site based on a phase shift between a modulated detection signal, a detection signal from the optical detector is modulated at a second frequency, and a reference signal having a difference frequency equal to the difference between the first frequency and the second frequency; and a position moving mechanism moves at least one of a position at which the intensity-modulated light is emitted by the light projection unit and the position at which the return light is incident on the light receiving unit.

18 Claims, 26 Drawing Sheets

U.S. PATENT DOCUMENTS

| | | | |
|---|---|---|---|
| 6,078,833 A | 6/2000 | Hueber | |
| 6,134,460 A * | 10/2000 | Chance | 600/342 |
| 6,149,598 A * | 11/2000 | Tanaka | 600/462 |
| 6,404,497 B1 * | 6/2002 | Backman et al. | 356/369 |
| 6,405,070 B1 * | 6/2002 | Banerjee | 600/407 |
| 6,461,304 B1 * | 10/2002 | Tanaka et al. | 600/462 |
| 6,516,209 B2 * | 2/2003 | Cheng et al. | 600/323 |
| 6,526,309 B1 * | 2/2003 | Chance | 600/473 |
| 6,564,087 B1 * | 5/2003 | Pitris et al. | 600/478 |
| 6,587,703 B2 * | 7/2003 | Cheng et al. | 600/310 |
| 6,801,648 B2 * | 10/2004 | Cheng | 382/134 |
| 6,984,205 B2 * | 1/2006 | Gazdzinski | 600/160 |
| 7,087,014 B2 * | 8/2006 | Sasaki | 600/178 |
| 7,414,729 B2 * | 8/2008 | Xie et al. | 356/484 |
| 7,418,169 B2 * | 8/2008 | Tearney et al. | 385/25 |
| 2005/0124875 A1 * | 6/2005 | Kawano et al. | 600/407 |
| 2006/0114473 A1 * | 6/2006 | Tearney et al. | 356/479 |
| 2007/0073162 A1 * | 3/2007 | Tearney et al. | 600/476 |
| 2010/0168588 A1 * | 7/2010 | Matsumoto et al. | 600/478 |

FOREIGN PATENT DOCUMENTS

| | | |
|---|---|---|
| JP | 06-209906 | 8/1994 |
| JP | 8-509880 | 10/1996 |
| JP | 10-500338 | 1/1998 |
| JP | 11-344442 | 12/1999 |
| JP | 2000-126116 | 5/2000 |
| WO | WO 94/21173 | 9/1994 |

* cited by examiner

IN-VIVO INFORMATION MEASUREMENT APPARATUS

BACKGROUND OF THE INVENTION

1. Field of the Invention

The present invention relates to an in-vivo information measurement apparatus that measures in-vivo information based on the concentration of biological tissue components in a living organism, such as oxygen concentration and hemoglobin concentration.

2. Description of Related Art

A conventionally known body-cavity examination probe includes a plurality of light sources and optical detectors at the tip thereof, as disclosed in U.S. Pat. No. 6,134,460 (FIG. 14A etc.). This probe includes two light sources disposed at a surface placed in contact with a surface inside the body cavity by inflating a balloon and an optical detector disposed at the center of these light sources.

However, the size of this type of body-cavity examination probe is limited in order to insert it into the body cavity, and the size of the surface placed in contact with the surface inside the body cavity is also limited. Therefore, it is difficult to provide a large number of light sources and optical detectors. As a result, the acquired measurement results are restricted to a single point, and therefore, there is a drawback in that carrying out measurement over a wide area inside the body cavity or over a specific region in the depth direction from the surface inside the body cavity takes a long time to complete.

BRIEF SUMMARY OF THE INVENTION

In light of the circumstances described above, it is an object of the present invention to provide an in-vivo information measurement apparatus that can measure over a wide area inside a body cavity in a short period of time, and that is capable of two-dimensional or three-dimensional imaging.

In order to achieve the object described above, the present invention provides the following solutions.

According to one aspect, the present invention provides an in-vivo information measurement apparatus comprising an insertion part for insertion into a body cavity; a light projection unit, provided at a tip of the insertion part, that irradiates an examination site inside the body cavity with intensity-modulated light which is intensity modulated at a first frequency; a light receiving unit that receives return light from the examination site at a different position from the light projection unit; an optical detector that detects return light from the examination site, which is received at the light receiving unit; an in-vivo information calculation unit that calculates in-vivo information for the examination site based on a phase shift between a modulated detection signal, formed by modulating a detection signal from the optical detector at a second frequency, and a reference signal having a difference frequency equal to the difference between the first frequency and the second frequency; and a position moving mechanism that moves at least one of a position at which the intensity-modulated light is emitted by the light projection unit and the position at which the return light is incident on the light receiving unit.

According to this aspect of the invention, the intensity-modulated light that is modulated at the first frequency irradiates the examination site from the light projection unit provided at the tip of the insertion part. After passing through the examination site, the emitted intensity-modulated light is incident as return light on the light receiving unit, which is disposed at a different position from the light projection unit, and is detected in the optical detector. The detection signal forms a modulated detection signal by being modulated at the second frequency, giving the phase shift from the reference signal, which has a difference frequency equal to the difference between the first frequency and the second frequency. Then, the in-vivo information for the examination site is calculated by operating the in-vivo information calculation unit based on this phase shift.

In this case, by operating the position moving mechanism, at least one of the position where the intensity-modulated light is emitted from the light projection unit and the position where the return light is incident on the light receiving unit is moved. When the emission position and the incident position are moved simultaneously while maintaining the same distance therebetween, the penetration depth of the intensity-modulated light into the examination site does not change, and therefore, it is possible to measure a one-dimensional or a two-dimensional distribution of the in-vivo information at a constant depth in the examination site. Also, by fixing one of the emission position and the incident position and moving the other one, when the distance between them changes, the penetration depth of the intensity-modulated light into the examination site also changes. Therefore, it is possible to measure the distribution of in-vivo information in the depth direction of the examination site. In such cases, since the emission position and the incident position of the light projection unit and the light receiving unit move, it is not necessary to provide a plurality of light projection units and light receiving units, which allows them to be housed in the tip of an insertion part of limited size, and therefore, it is possible to make the apparatus more compact. In addition, since the movement of the emission position or the incident position is achieved by operating the position moving mechanism, it is not necessary to move the entire insertion part, which allows measurement of in-vivo information to be carried out over a wide area in a short period of time.

In the aspect of the invention described above, the insertion part may be an endoscope.

In the aspect of the invention described above, the insertion part may be an elongated probe.

The aspect of the invention described above may also include an illumination unit that irradiates the examination site with illumination light; an objective optical system that forms an image of the examination site; and an imaging unit that acquires the image formed by the objective optical system. The insertion part may include an endoscope and an elongated probe, and the elongated probe may be disposed inside the endoscope.

According to this aspect of the invention, when the endoscope is inserted into the body cavity and the illumination unit is operated, the examination site is irradiated with illumination light, and an image of the examination site formed by the objective optical system is acquired by operating the imaging unit. Thus, an endoscope image is acquired. Moreover, since the probe of the in-vivo information measurement apparatus is disposed inside the endoscope, measurement of the in-vivo information at the examination site is carried out. In other words, it is possible to simultaneously acquire an endoscope image and in-vivo information of the same examination site.

In the aspect of the invention described above, at least one of the light projection unit and the light receiving unit is preferably disposed inside the field of view of the objective optical system.

With this configuration, it is possible to visually confirm which position of the examination site is being measured by observing the endoscope image.

The aspect of the invention described above may also include an image combining device that superimposes the endoscope image obtained by the endoscope and in-vivo information for the examination site calculated by the in-vivo information calculation unit.

With this configuration, it is possible to confirm the measurement by associating the endoscope image and the in-vivo information of the examination site, which are combined by the image combining device.

In the aspect of the invention described above in which the insertion part is an elongated probe, this probe can be inserted into a channel of the endoscope.

By inserting the probe into a channel of the endoscope, when the endoscope is inserted into the body cavity, the probe is also inserted into the cavity. This enables two-dimensional or three-dimensional in-vivo information measurement to be carried out in the vicinity of the examination site observed with the endoscope.

The aspect of the invention described above may also include a plurality of optical fibers in the insertion part. In this case, at least one of the light projection unit and the light receiving unit is constituted by end faces of the optical fibers, and the position moving mechanism includes an optical fiber selection mechanism that selects an optical fiber for guiding intensity-modulated light to be irradiated or return light to be detected.

In such a case, the optical fiber that guides the intensity-modulated light to be irradiated or the return light to be detected is selected by operating the optical fiber selection mechanism. For example, by fixing the light projection unit and sequentially selecting optical fibers that guide the return light to be detected, it is possible to change the distance between the light projection unit and the light receiving unit. In the same way, by fixing the light receiving unit and sequentially selecting optical fibers that guide the intensity-modulated light to be irradiated, it is possible to change the distance between the light projection unit and the light receiving unit. When the distance between them changes, the penetration depth of the intensity-modulated light into the examination site changes, and it is thus possible to measure the distribution of in-vivo information in the depth direction of the examination site.

By operating the optical fiber selection mechanism to sequentially change the light projection unit and the light receiving unit while maintaining the same distance therebetween, the penetration depth of the intensity-modulated light into the examination site does not change. Therefore, it is possible to measure the one-dimensional or two-dimensional distribution of in-vivo information at a constant depth in the examination site. In such a case, this is achieved simply by changing the light projection unit or the light receiving unit by operating the optical fiber selection mechanism, and therefore, it is possible to carry out measurement of the in-vivo information over a wide area in a short period of time.

In the aspect of the invention described above, the light projection unit and the light receiving unit are preferably both constituted by the end face of a common optical fiber.

By radiating the intensity-modulated light or receiving the return light from the examination site using a common optical fiber, the number of optical fibers can be reduced, which allows the insertion part to be inserted into the body cavity to be made thin and a compact structure to be achieved.

In the aspect of the invention described above, the plurality of optical fibers are preferably formed of a fiber bundle.

Since it is possible to increase the fiber core density using an optical fiber bundle, the apparatus can be formed even more compactly.

In the aspect of the invention described above, the light projection unit is preferably constituted by an end face of one of the optical fibers. In addition, the optical fiber selection mechanism may include a scanning mirror that varies the angle at which the intensity-modulated light is reflected to select the optical fiber into which the intensity-modulated light is introduced.

With this scanning mirror, it is possible to make the intensity-modulated light incident on any optical fiber simply by changing the angle of the mirror.

In the aspect of the invention described above, the light receiving unit is preferably constituted by an end face of one of the optical fibers. In addition, the optical fiber selection mechanism may include a scanning mirror that varies the angle at which light is received at the light receiving unit and the angle at which return light transmitted through the optical fiber is reflected to selectively introduce the return light to the optical detector.

With this scanning mirror, it is possible to introduce the return light transmitted through any optical fiber into the optical detector simply by changing the angle of the mirror.

In the aspect of the invention described above, the scanning mirror may be formed of a galvano mirror or it may be formed of a MEMS (Micro Electro Mechanical System) mirror array.

In the aspect of the invention described above, the position moving mechanism may include a moving mechanism that moves the light projection unit or the light receiving unit over a surface inside the body cavity.

Since the light projection unit or the light receiving unit is moved over the body cavity surface by operating the moving mechanism, it is possible to measure the distribution of in-vivo information over the body cavity surface. It is therefore possible to measure the distribution over a region even if a single or a small number of light projection units and light receiving units are provided, which allows the apparatus to be made more compact as well as improving the measurement efficiency.

In the aspect of the invention described above, the moving mechanism may rotate the light projection unit or the light receiving unit about an axis of the endoscope, or it may translate the light projection unit or the light receiving unit along an axis of the endoscope.

With this configuration, it is possible to measure the two-dimensional or three-dimensional distribution of in-vivo information by moving the light projection unit or the light receiving unit over the body cavity surface in the circumferential direction and the longitudinal direction.

In the aspect of the invention described above, the position moving mechanism may include a scanning mirror that reflects the intensity-modulated light to scan the examination site.

The emission position of the intensity-modulated light to the examination site is changed by changing the angle of the scanning mirror. As a result, similarly to moving the light projection unit itself, it is possible to measure the in-vivo information over a wide region while reducing the number of light projection units required, which allows the apparatus to be made more compact and improves the measurement efficiency.

In the aspect of the invention described above, the in-vivo information measurement system may also include an in-vivo information display unit that displays in-vivo information for the examination site, which is calculated by the in-vivo information calculation unit.

By operating the in-vivo information display unit, it is possible to visualize the calculated in-vivo information, and a multi-dimensional distribution can be displayed as an image.

In the aspect of the invention described above, the insertion part is preferably an endoscope, and the in-vivo information display unit simultaneously displays an image of the surface of the examination site, which is acquired by the endoscope, and the in-vivo information for the examination site.

With this configuration, it is possible to display an image of the surface of the examination site acquired with the endoscope and the distribution of in-vivo information in the interior in such a manner that they are associated with each other, which allows an affected region in the examination site to be easily identified.

In the aspect of the invention described above, the in-vivo information display unit may multi-dimensionally display the in-vivo information for the examination site.

By displaying the in-vivo information multi-dimensionally, it is possible to indicate the condition of an affected region in the examination site in an easily understandable manner.

The aspect of the invention described above may also include a wavelength selection mechanism, between the light receiving unit and the optical detector, for selectively detecting in the optical detector light of a predetermined wavelength among the return light.

With the wavelength selection mechanism, it is possible to selectively detect only light of a specific wavelength among the light received in the light receiving unit using the optical detector. For example, when irradiating excitation light and observing the fluorescence produced from the examination site, the light received in the light receiving unit may include reflected excitation light in addition to the fluorescence. In such a case, only the fluorescence can be selectively detected in the optical detector by means of the wavelength selection mechanism.

In the aspect of the invention described above, the wavelength selection mechanism may be formed of a dichroic mirror, or it may be formed of a filter that transmits only fluorescence or phosphorescence among the return light.

In the aspect of the invention described above, the optical detector may be formed of a photodetector array.

In the aspect of the invention described above, the optical detector may be formed of a charge coupled device (CCD).

The aspect of the invention described above may also include a light source and a modulator that intensity modulates light from the light source at a first frequency, wherein the light source is constructed so as to be capable of emitting a plurality of different wavelengths of light.

By using light of a plurality of wavelengths, it is possible to obtain the absolute values of the scattering coefficient and the absorption coefficient, which enables measurement of the concentration of biological tissue components based on these values.

In the aspect of the invention described above, the in-vivo information may be the concentration of biological tissue components. Also, the biological tissue components may be any of oxygen, hemoglobin, oxygenated hemoglobin, deoxygenated hemoglobin, water, and carbon dioxide.

In another aspect, the present invention provides an in-vivo information measurement apparatus comprising a light projection unit that irradiates an examination site inside a body cavity with intensity-modulated light which is intensity modulated at a first frequency; a light receiving unit that receives return light from the examination site at a different position from the light projection unit; an optical detector that detects the return light received in the light receiving unit; an in-vivo information calculating unit that calculates in-vivo information for the examination site based on a phase shift between a modulated detection signal, formed by modulating a detection signal from the optical detector at a second frequency, and a reference signal having a difference frequency equal to the difference between the first frequency and the second frequency; and an optical scanning unit that scans at least one of the intensity-modulated light from the light projection unit and the return light from the light receiving unit.

According to this aspect of the invention, the intensity-modulated light that is modulated at the first frequency is emitted towards the examination site inside the body cavity from the light projection unit. After passing through the examination site, the radiated intensity-modulated light is incident as return light on the light receiving unit, which is disposed at a different position from the light projection unit, and is detected in the optical detector. The detected detection signal forms a modulated detection signal by being modulated at the second frequency, and gives the phase shift of the reference signal, which has a difference frequency equal to the difference between the first frequency and the second frequency. Then, the in-vivo information for the examination site is calculated by operating the in-vivo information calculation unit based on this phase shift.

By scanning at least one of the intensity-modulated light in the light projection unit and the return light in the light receiving unit using the optical scanning unit, it is possible to measure the in-vivo information over a wide area while reducing the number of light projection units required, similarly to moving the light projection unit itself, which allows the apparatus to be made more compact and the measurement efficiency to be improved.

In the aspect of the invention described above, the scanning unit may be a scanning mirror.

In the aspect of the invention described above, at least one of the light projection unit and the light receiving unit may be constituted by end faces of optical fibers; and an optical fiber for guiding the intensity-modulated light to be irradiated or the return light to be detected is selected by the scanning mirror.

In the aspect of the invention described above, the scanning mirror may be formed of a MEMS mirror array.

In the aspect of the invention described above, the in-vivo information measurement apparatus may also include an insertion part that can be inserted into the body cavity.

In the aspect of the invention described above, the optical scanning unit may be provided at a tip of the insertion part.

In the aspect of the invention described above, the optical scanning unit may be provided on the outer side of the insertion part.

According to the present invention, an advantage is afforded in that it is possible to easily and efficiently measure the distribution of in-vivo information in directions in the plane of the examination site and in the depth direction of the examination site over a comparatively wide region with a compact configuration, and without requiring a large area where it is inserted into the body cavity.

DETAILED DESCRIPTION OF THE INVENTION

First Embodiment

A description of an in-vivo information measurement apparatus 1 according to a first embodiment of the present invention will be given below with reference to FIGS. 1 to 4.

Figure 1:
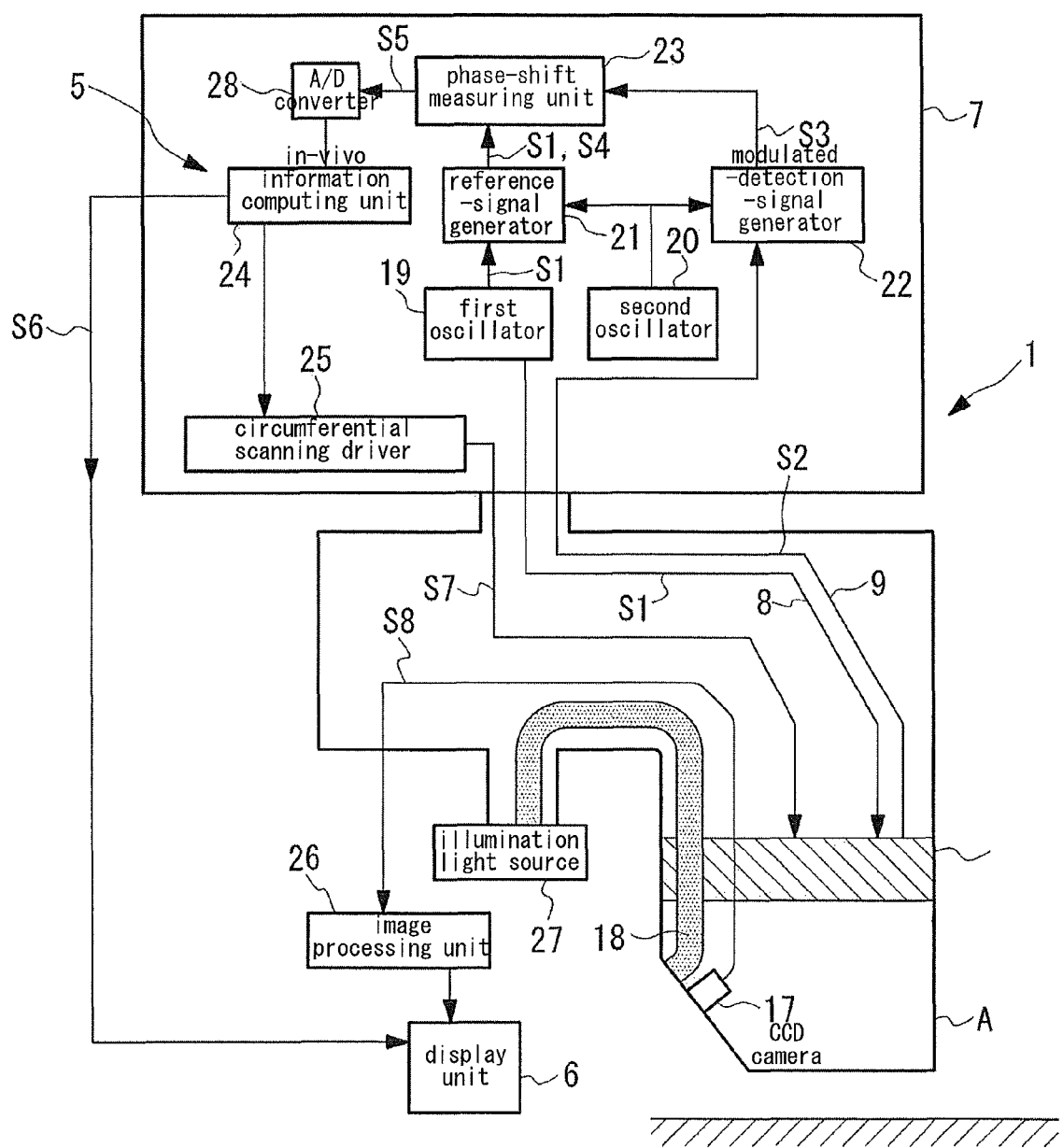
FIG. 1 is an overall schematic diagram showing an in-vivo information measurement apparatus according to a first embodiment of the present invention.
Figure 2:
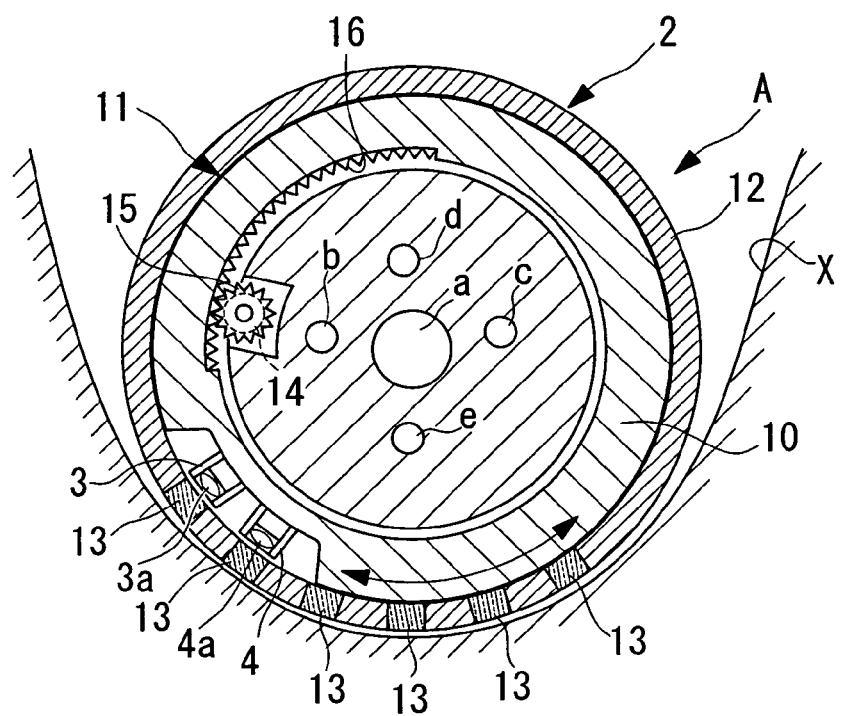
FIG. 2 is a cross-sectional diagram showing a measurement head unit in the in-vivo information measurement apparatus of FIG. 1.

The in-vivo information measurement apparatus 1 according to this embodiment is typically inserted into a body cavity and is provided at the tip of an insertion part A of an endoscope for carrying out examination of a surface X inside the body cavity. As shown in FIGS. 1 and 2, the in-vivo information measurement apparatus 1 includes a measurement head unit 2 disposed at the tip of the insertion part A; a light source unit 3, provided in the measurement head unit 2, for irradiating light towards the surface X inside the body cavity; an optical detection unit 4, provided in the measurement head unit 2, that detects light returning from tissue inside the body cavity; a computation unit 5 that computes in-vivo information based on the light detection signal detected in the optical detection unit 4, for example, the oxygen concentration, hemoglobin concentration, water content, carbon dioxide concentration, absorption coefficient, scattering coefficient, and so on, of the tissue; and a display unit 6 that displays the computed in-vivo information.

The light source unit 3 is formed, for example, of a laser diode and emits laser light of a specified frequency. The optical detection unit 4 is a photodiode, for example. Reference numerals 3a and 4a represent lenses. With these lenses, the light source unit 3 serves as light projection unit projecting light towards the body cavity surface X, and the optical detection unit 4 serves both as a light receiving unit and detector of light returning from the tissue.

The computation unit 5 and the display unit 6 are disposed outside the body. The computation unit 5 is disposed inside a processing apparatus 7 outside the body. The processing apparatus 7 and the light source unit 3 inside the measurement head unit 2 are connected by a cable 8. The processing apparatus 7 is also connected to the optical detection unit 4 in the measurement head unit 2 via a cable 9. The cables 8 and 9 pass through the inside of the tubular insertion part A constituting the endoscope, and extend to the tip of the endoscope.

As shown in FIG. 2, the measurement head unit 2 includes a cylindrical movable member 10 disposed at the tip of the insertion part A and a moving mechanism 11 that moves the movable member 10 in the circumferential direction. The light source unit 3 and the optical detection unit 4 are fixed to the movable member 10 with a predetermined space therebetween in the circumferential direction.

The movable member 10 is supported at the inner side of a tubular cover member 12, which is disposed at the outermost periphery of the insertion part A, and is supported in such a manner as to be movable in the circumferential direction. The cover member 12 includes, for example, a plurality of transparent window portions 13 disposed with gaps therebetween in the circumferential direction. When the light source unit 3 becomes aligned with one of these window portions 13, the optical detection unit 4 is disposed so as to always be aligned with another one of the window portions 13.

The moving mechanism 11 includes, for example, a motor 14 disposed at the inner side of the movable member 10; a drive gear 15 that is driven about an axis parallel to the axis of the endoscope by the motor 14; and a follower gear 16 attached to the inner circumferential surface of the movable member 10 so as to mesh with the drive gear 15. When the motor 14 is driven to rotate the drive gear 15, the movable member 10 is rotationally driven about the axis of the endoscope via the follower gear 16, which is meshed with the drive gear 15.

Reference characters a to e in FIG. 2 indicate channels for passing, for example, a cable to a CCD camera 17, and for passing a light guide 18, a nozzle, or forceps, for instance.

As shown in FIG. 1, the processing apparatus 7 includes a first oscillator 19, a second oscillator 20, a reference-signal generator 21, a modulated-detection-signal generator 22, a phase-shift measuring unit 23, and an in-vivo information computing unit 24. The first oscillator 19 causes intensity-modulated light S1, modulated at a first frequency of, for example, 200 MHz, to be emitted from the light source unit 3. The second oscillator 20 generates a second frequency, for example, 200.05 MHz. The modulated-detection-signal generator 22 modulates a detection signal S2 detected by the optical detection unit 4 at the second frequency generated by the second oscillator 20 to create a modulated detection signal S3.

The reference-signal generator 21 generates a reference signal S4 with a difference frequency equal to the difference between the first frequency and the second frequency. The phase-shift measuring unit 23 measures a phase shift S5 between the reference signal S4 and the modulated detection signal S3 detected by the optical detection unit 4 and modulated at the second modulation frequency. The in-vivo information computation unit, constituted of a computer 24, calculates in-vivo information S6 based on the modulated detection signal S3, the intensity-modulated light signal S1, and the phase shift S5.

Operational commands for the moving mechanism 11 are output from the computer 24. Reference numeral 25 represents a circumferential scanning driver that is connected to the computer 24 and that outputs a control signal S7 for controlling the motion of the movable member 10 in the circumferential direction.

Figure 3:
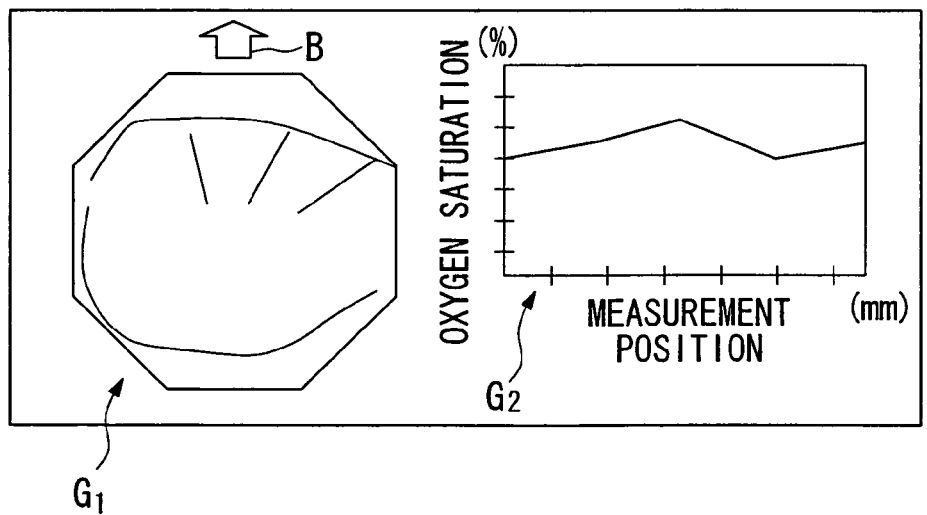
FIG. 3 shows an example screen display of a measurement image obtained by the in-vivo information measurement apparatus in FIG. 1.

The display unit 6, which is a monitor, is connected to the computer 24 and is also connected to an image processing unit 26 that processes the image signal S8 captured by an image-capturing unit, such as a CCD camera 17 or the like, disposed at the tip of the endoscope. As shown in FIG. 3 for example, an image G1 of a surface inside the body, which is subjected to image processing by the image processing unit 26, and a graph G2 showing the in-vivo information calculated by the computer 24 are simultaneously displayed on the monitor screen. As shown in FIG. 3 for example, in-vivo information such as oxygen saturation or the like is shown on the vertical axis, and the horizontal axis indicates the position along the circumferential direction of the endoscope.

Arrow B in the figure indicates in which direction of the endoscope image G1 is the in-vivo information shown by graph G2.

The operation of the in-vivo information measurement apparatus 1 according to this embodiment, having such a configuration, will be described below.

To measure the in-vivo information using the in-vivo information measurement apparatus 1 according to this embodiment, the insertion part A of the endoscope is inserted into the body cavity, and the measurement head unit 2 disposed at the tip of the insertion portion A is brought into contact with the vicinity of an infected area on the surface X in the body cavity. At the tip of the insertion portion A, illumination light guided by the light guide 18 from an externally provided illumination light source 27 and the condition of the surface X inside the body cavity are observed by the CCD camera 17 disposed in the vicinity thereof.

The operator determines whether or not the measurement head unit 2 is disposed in the vicinity of the infected area while viewing the endoscope image G1 captured by the CCD camera 17 on the display unit 6, and when he or she determines that it is disposed in the vicinity of the infected part, he or she operates the in-vivo information measurement apparatus 1 according to this embodiment.

First, the light source unit 3 and the optical detection unit 4 provided in the measurement head unit 2 are positioned at the end of the measurement range in the circumferential direction. At this point, the light source unit 3 and the optical detection unit 4 are disposed so as to be aligned with the window portions 13 in the cover member.

Next, by operating the first oscillator 19 in the processing apparatus 7, the intensity-modulated light S1, modulated at the first frequency, is emitted from the light source unit 3 and is directed towards the surface X inside the body cavity via one of the window portions 13. The emitted light enters the tissue from the body cavity surface X, and after being transmitted through or diffused in the tissue, it passes through another window portion 13 disposed at a certain distance in the circumferential direction and is detected by the optical detection unit 4, which is disposed inside the cover member 12. Since the distance between the window members 13 is fixed, the light emitted from the light source unit 3 is detected by the optical detection unit 4 after penetrating to a fixed depth inside the tissue. Therefore, it is detected as a signal that includes in-vivo information of the tissue disposed at a fixed depth below the body cavity surface X.

The reference signal S4 having a frequency equal to the difference between the first and second frequencies produced by the first and second oscillators, respectively, is generated by the reference-signal generator 21. The reference signal S4 obtained is input to the phase-shift measuring unit 23 together with the intensity-modulated light signal S1. Also, by modulating the obtained detection signal S2 at the second frequency in the modulated-detection-signal generator 22, the modulated detection signal S3 is produced and is input to the phase-shift measuring unit 23. The phase shift S5 between the input reference signal S4 and the modulated detection signal S3 is measured in the phase-shift measuring unit 23 and is then output. The measured phase shift S5, the intensity-modulated optical signal S1 and the modulated detection signal S3 are converted to digital data by an A/D converter 28 and are input to the in-vivo information computation unit in the computer 24.

The in-vivo information S6, such as the oxygen saturation level, for example, is computed in the in-vivo information computation unit based on the input phase-shift S5, the intensity-modulated optical signal S1, and the modulated detection signal S3. Therefore, the computed in-vivo information S6 and the positional information of the optical detection unit 4 along the circumferential direction are displayed on the display unit 6.

Then, by operating the motor 14 of the moving mechanism 11 to rotationally drive the drive gear 15 and rotate the follower gear 16, which is meshed with the drive gear 15, about the axis of the endoscope, the movable member 10 is rotated in the circumferential direction inside the cover member 12. By doing so, the movable member 10 is moved in the circumferential direction while maintaining a predetermined spacing between the light source unit 3 and the optical detection unit 4, which are attached to the movable member 10.

When the light source unit 3 and the optical detection unit 4 are operated by rotating the movable member 10 in the circumferential direction, the light source unit 3 and the optical detection unit 4 deviate from the window members 13 provided in the cover member 12, and therefore, irradiation of the intensity-modulated light S1 towards the body cavity surface X and detection of the light returning from the body are interrupted until the light source unit 3 and the optical detection unit 4 reach the next positions where they are aligned with the window portions 13. Then, once the light source unit 3 and the optical detection unit 4 are moved to the position where they are aligned with the next window portions 13, the intensity-modulated light S1 is again irradiated towards the body cavity surface X at a different position in the circumferential direction, and the return light is detected by the optical detection unit 4.

By operating the moving mechanism 11 in this way, the light source unit 3 and the optical detection unit 4 are moved in the circumferential direction, and by measuring the in-vivo information S6 at a plurality of different points in the circumferential direction, the graph G2 shown in FIG. 3 is displayed on the display unit 6. The operator can thus determine the condition of an affected area while comparing the endoscope image G1 of the body cavity surface X and the in-vivo information graph G2, which are displayed simultaneously.

In such a case, with the in-vivo information measuring apparatus 1 according to this embodiment, it is possible to measure the in-vivo information S6 at different circumferential positions while moving the light source unit 3 and the optical detection unit 4 in the circumferential direction by operating the moving mechanism 11. Therefore, it is not necessary to provide a plurality of light source units 3 and optical detection units 4 at the tip of the insertion part A, which is of limited size, and therefore, it is possible to construct the tip of the insertion part A with a compact configuration. Also, an advantage is afforded in that it is possible to easily and efficiently measure the distribution of in-vivo information S6 along the circumferential direction inside the body cavity simply by moving the light source unit 3 and the optical detection unit 4 in the circumferential direction.

Figure 4:
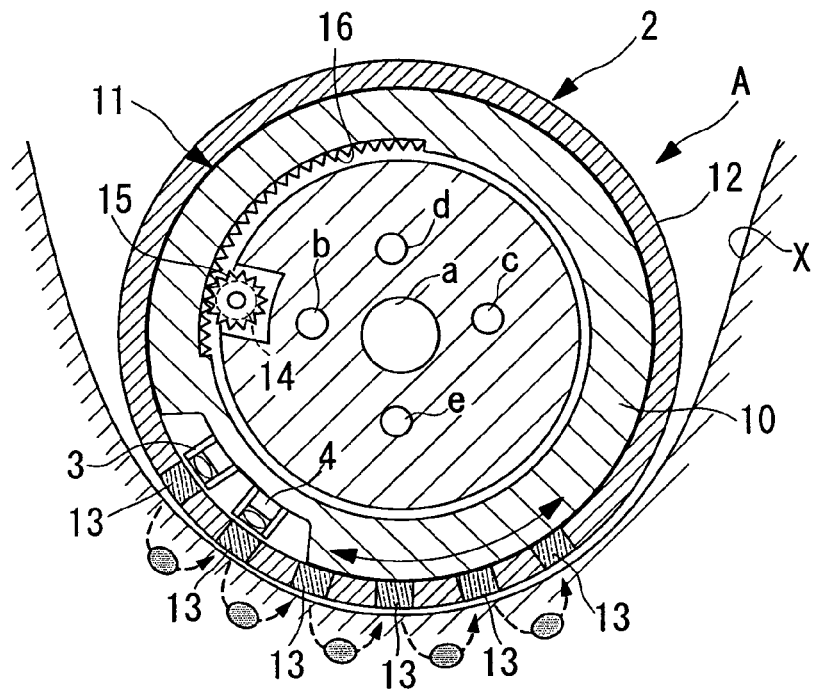
FIG. 4 is a cross-sectional diagram showing an example of the operation of the in-vivo information measurement apparatus in FIG. 1.

Furthermore, since the light source unit 3 and the optical detection unit 4 are moved simultaneously while maintaining a fixed distance therebetween, as shown in FIG. 4, it is possible for the light beams to penetrate to substantially the same depth at each circumferential position inside the body cavity, which allows a one-dimensional distribution of the in-vivo information S6 at a fixed depth to be obtained.

Figure 5:
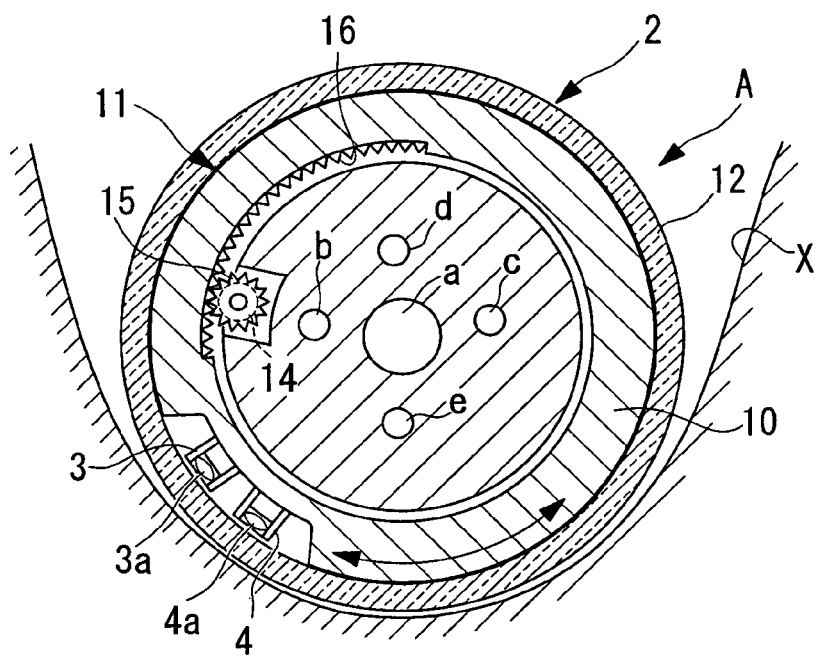
FIG. 5 is a cross-sectional diagram showing a modification of the in-vivo information measurement apparatus in FIG. 1.
Figure 6:
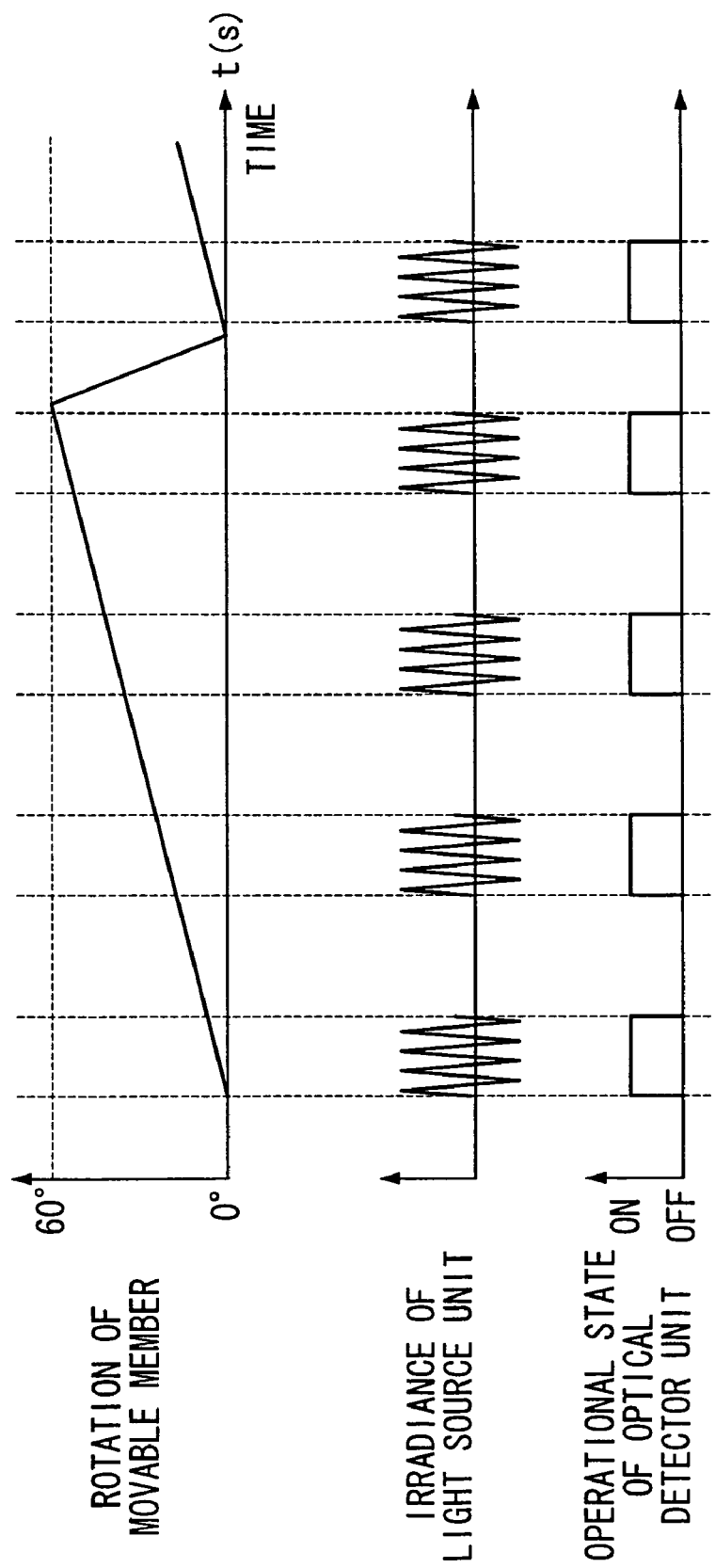
FIG. 6 is a timing diagram of the operation of a movable member by the in-vivo information measurement apparatus in FIG. 5 and the operational timing of a light source unit and an optical detection unit.

In the in-vivo information measurement apparatus 1 according to this embodiment, the plurality of window portions 13 are disposed in the cover member 12 with gaps therebetween in the circumferential direction, and thus the circumferential positions on the body cavity surface X where the intensity-modulated light S1 is incident can be changed only in a restricted manner. Instead of this, however, as shown in FIG. 5, the cover member 12 may be entirely formed of a transparent material, and as shown in FIG. 6, the light source unit 3 and the optical detection unit 4 may be operated intermittently.

In this case, by synchronizing the movement of the light source unit 3 and the optical detection unit 4 in the circumferential direction due to the movable member 10 and the operating timing of the light source unit 3 and the optical detection unit 4, it is possible to obtain a one-dimensional distribution of the in-vivo information S6 in the same way as in the above-described embodiment.

In the description given above, an example is given in which a laser diode is fixed to the movable member 10 of the measurement head 2 as the light source unit 3; however, instead of this, light may be guided from an externally provided laser light source via a light guiding unit (first light guiding unit), such as an optical fiber. Moreover, in the description above, an example is described in which a photodiode is fixed to the movable member 10 of the measurement head 2 as the optical detection unit 4; however, instead of this, the photodiode may be disposed outside of the body and the light may be guided thereto via a light guiding unit (second light guiding unit), such as an optical fiber.

Second Embodiment

Next, a second embodiment of an in-vivo information measurement apparatus according to the present invention will be described with reference to FIGS. 7 to 9.

Parts in the description of this embodiment having the same configuration as those in the in-vivo information measurement apparatus 1 according to the first embodiment described above will be assigned the same reference numerals, and a description thereof shall be omitted here.

An in-vivo information measurement apparatus 30 according to this embodiment differs from the in-vivo information measurement apparatus 1 according to the first embodiment in that the light source unit 3 and the optical detection unit 4 are rotated about the axis of the endoscope and are also translated in a direction parallel to the axis of the endoscope.

Figure 7:
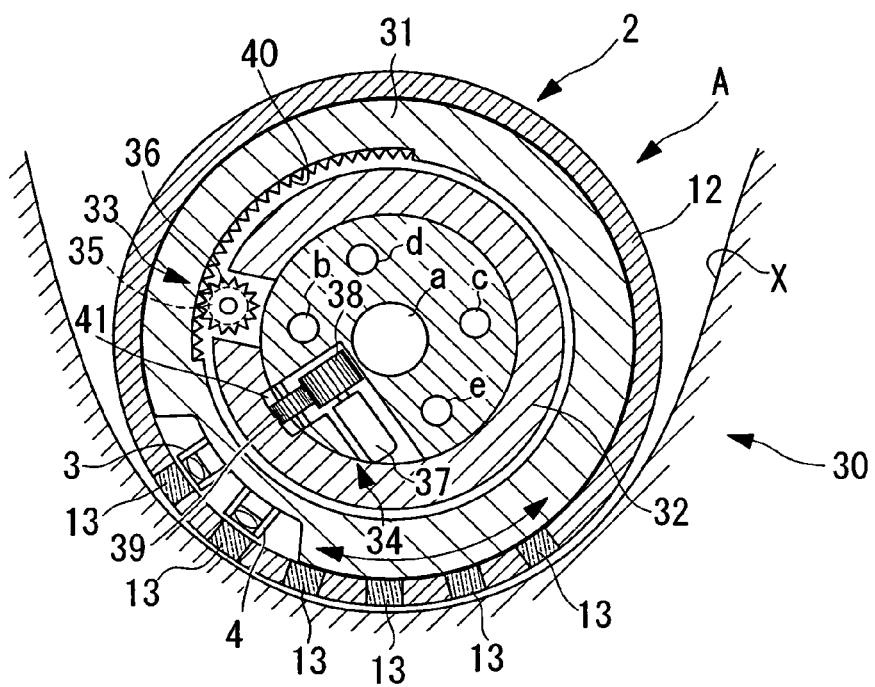
FIG. 7 is a cross-sectional diagram showing the measurement head unit in an in-vivo information measurement apparatus according to a second embodiment of the present invention.
Figure 8:
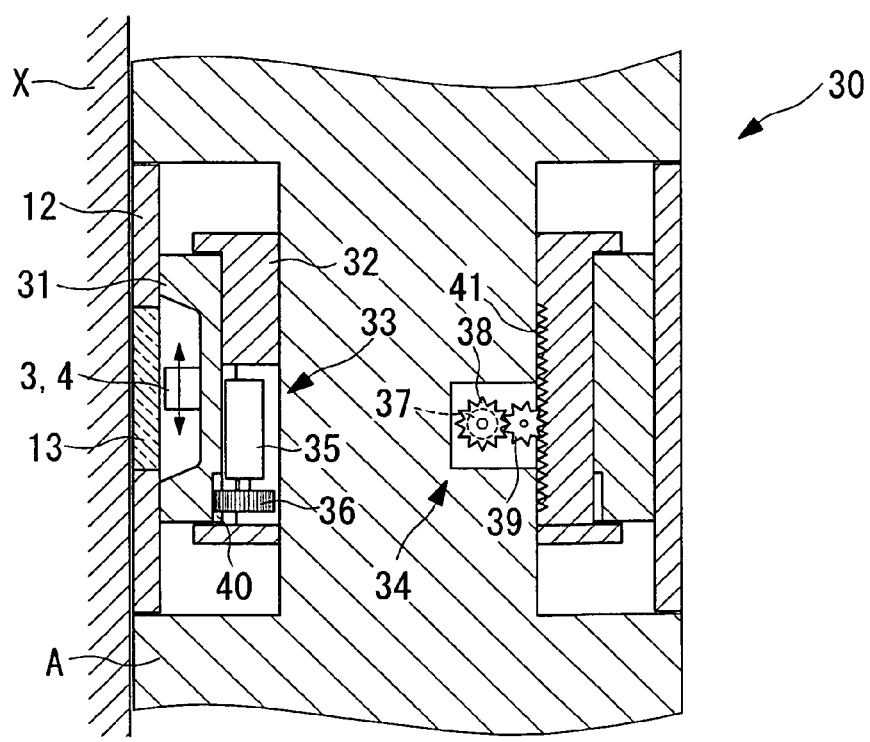
FIG. 8 is a longitudinal section showing the measurement head unit in FIG. 7.

More specifically, as shown in FIGS. 7 and 8, the in-vivo information measurement apparatus 30 according to this embodiment includes a first movable member 31 that is supported so as to be movable both in a direction parallel to the axis of the endoscope and in the circumferential direction; a second movable member 32 that is locked with respect to the relative motion in the axial direction and that is attached to the first movable member 31 so as to be capable of relative motion in the circumferential direction; a first moving mechanism 33, provided in the second movable member 32, that translates the first movable member 31 in the circumferential direction with respect to the second movable member 32; and a second moving mechanism 34 that moves both the first movable member 31 and the second movable member 32 in the axial direction. All of these elements are contained inside a cover member 12.

The first and second moving mechanisms 33 and 34 are formed of motors 35 and 37, drive gears 36, 38, and 39, and follower gears 40 and 41 provided in the first and second movable members 31 and 32, respectively.

Parts that are longer in the axial direction than those in the in-vivo information measurement apparatus 1 according to the first embodiment are used as the window portions 13 provided in the cover member 12.

Figure 9:
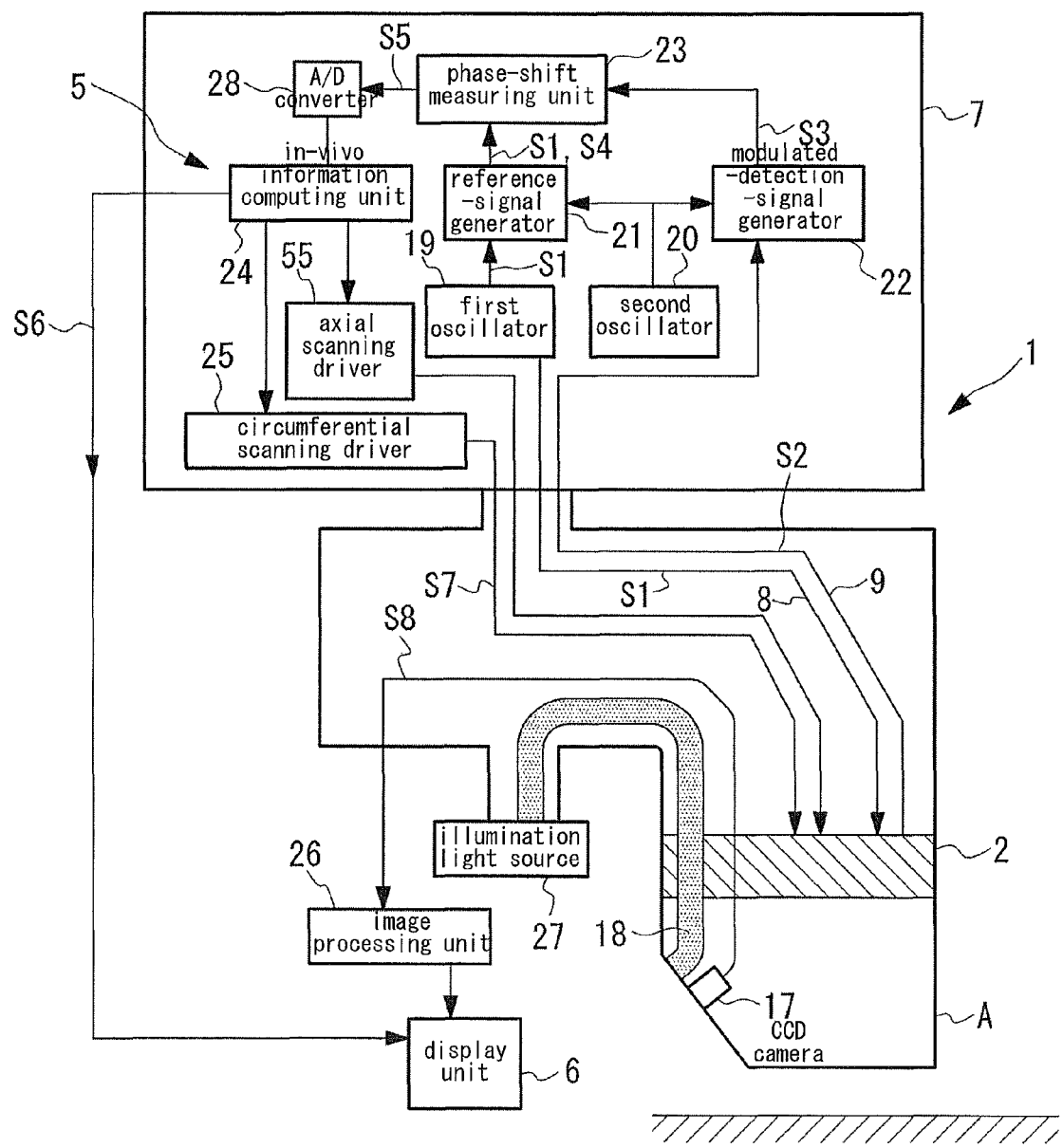
FIG. 9 is an overall schematic diagram showing the in-vivo information measurement apparatus in FIG. 7.

As shown in FIG. 9, the in-vivo information measurement apparatus 30 according to this embodiment is provide with an axial scanning driver 55, which is connected to the computer 24 in the processing apparatus 7.

To measure in-vivo information using the in-vivo information measurement apparatus 30 according to this embodiment, having such a configuration, the insertion part A of the endoscope is inserted inside the body cavity so as to bring the measurement head unit 2 disposed at the tip thereof into contact with a body cavity surface X at an infected area. Then, light is irradiated from the light source unit 3, and the return light is detected by the optical detection unit 4. By doing so, in-vivo information S6 about the tissue disposed at a predetermined depth from the body cavity surface X is measured. Subsequently, while moving the first movable member 31 in the circumferential direction of the endoscope by operating the first moving mechanism 33, a distribution of the in-vivo information S6 along the circumferential direction is measured, similarly to the first embodiment.

After measuring the circumferential distribution over a predetermined region, the second moving mechanism 34 is operated to move the first and second movable members 31 and 32 in the axial direction. Thus, by repeating this measurement procedure, it is possible to obtain the distribution of in-vivo information S6 over a two-dimensional region.

In the in-vivo information measurement apparatus 30 according to this embodiment, both the light source unit 3 and the optical detection unit 4 are fixed to the first movable member 31 and are made to move in the circumferential direction and the axial direction while constantly maintaining the same positional relationship therebetween. In this way, it is possible to obtain the distribution of in-vivo information S6 at a predetermined depth. Instead of this configuration, however, as shown in FIGS. 10 and 11 for example, the light source unit 3 may be fixed to the second movable member 32 and the optical detection unit 4 may be fixed to the first movable member 31.

Figure 12:
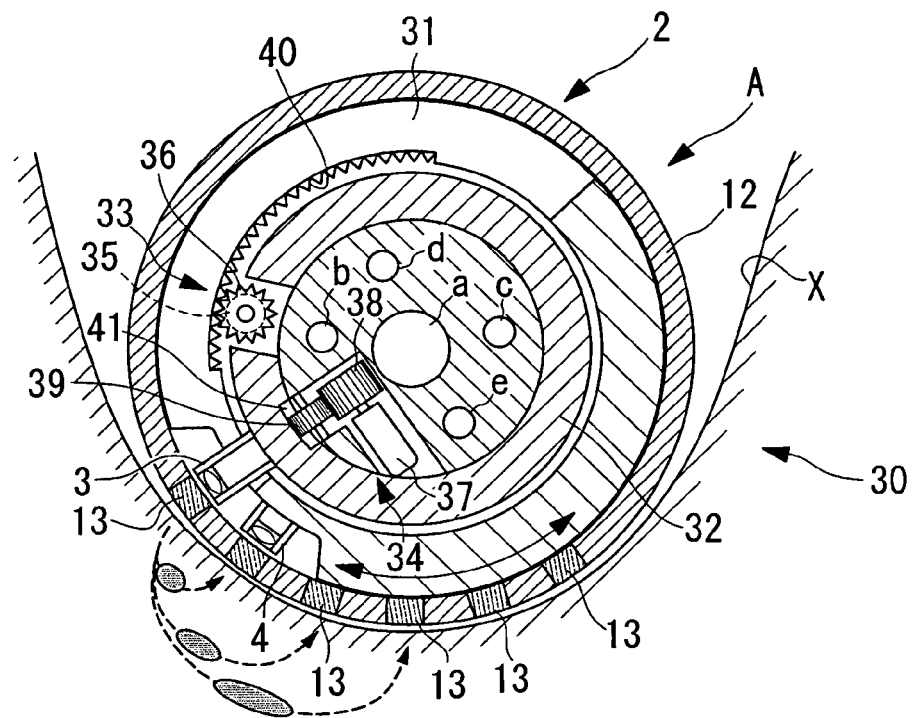
FIG. 12 is a cross-sectional diagram showing an example of the operation of the in-vivo information measurement apparatus in FIG. 10.
Figure 13:
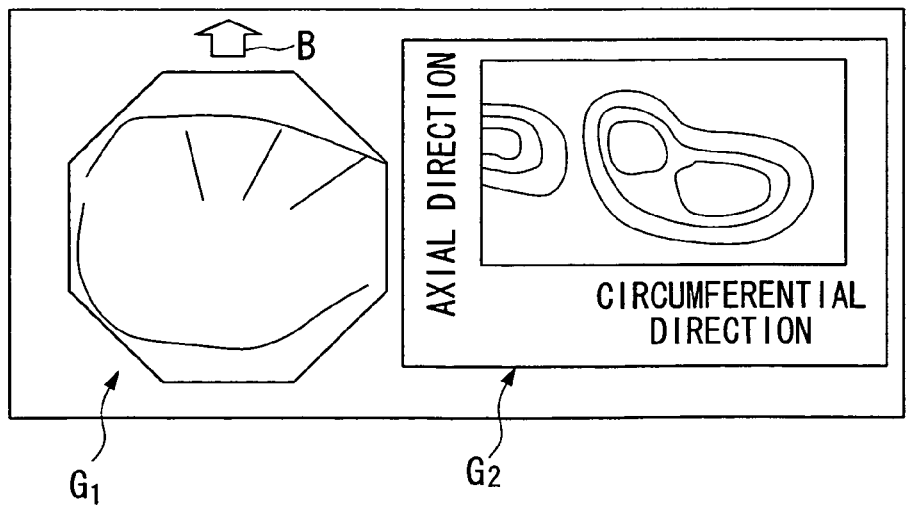
FIG. 13 shows an example of the screen display for a measurement image obtained by the in-vivo information measurement apparatus in FIG. 10.

In other words, the light source unit 3 is fixed at one window portion 13a to irradiate light from the same position, and the first movable member 31 is moved in the circumferential direction relative to the second movable member 32, so that a space is formed in the circumferential direction between the optical detection unit 4 and the light source unit 3. In this way, as shown in FIG. 12, it is possible to detect with the optical detection unit 4 light penetrating to a deeper position from the body cavity surface X, depending on the distance from the light source unit 3. Also, after the optical detection unit 4 is moved to a predetermined region in the circumferential direction, the second moving mechanism 34 is operated to move the first and second movable members 31 and 32 in the axial direction of the endoscope. Accordingly, as shown in FIG. 13, it is possible to obtain the distribution of in-vivo information S6 over a two-dimensional region of the body cavity surface X as well as three-dimensionally in the depth direction.

Figure 10:
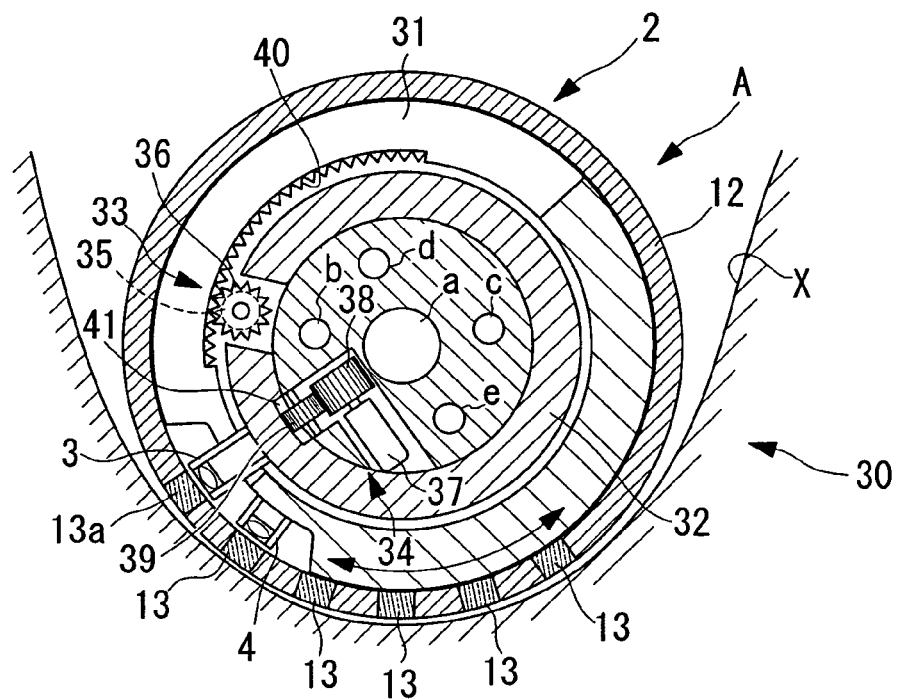
FIG. 10 is a cross-sectional diagram showing a modification of the in-vivo information measurement apparatus in FIG. 7.
Figure 11:
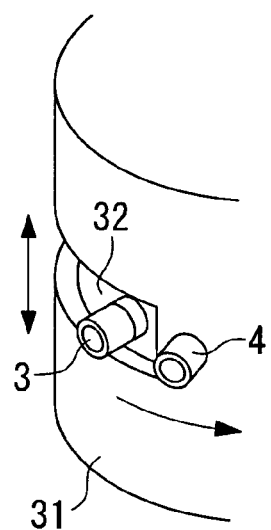
FIG. 11 is a perspective view for explaining a movable member in FIG. 10.
Figure 14:
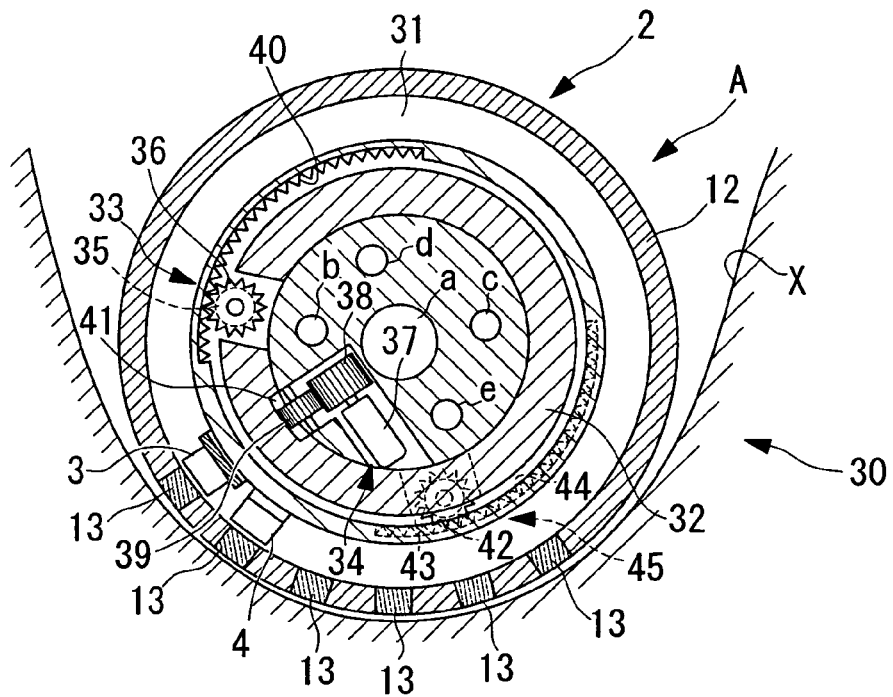
FIG. 14 is a cross-sectional diagram showing another modification of the in-vivo information measurement apparatus in FIG. 10.
Figure 15:
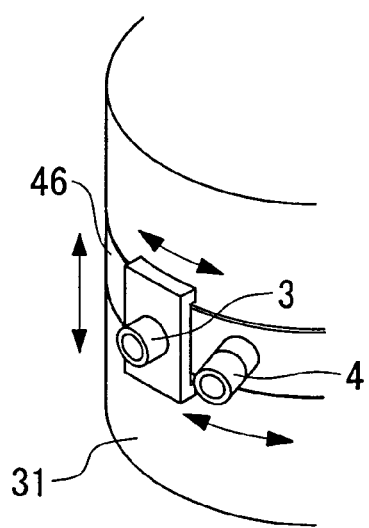
FIG. 15 is a perspective view for explaining a movable member in FIG. 14.

In the embodiment shown in FIG. 10, the position of the light source unit 3 in the circumferential direction is fixed; instead of this, however, as shown in FIGS. 14 and 15, a third moving mechanism 45 formed of a motor 42 and a driving gear 43 and follower gear 44 may be provided, a third movable member 46 that can relatively move in the circumferential direction relative to the first movable member 31 may be provided, and the optical detection unit 4 may be fixed to the third movable member 46. With this arrangement, it is possible to measure the three-dimensional distribution of in-vivo information S6 over a wider area.

Figure 16:
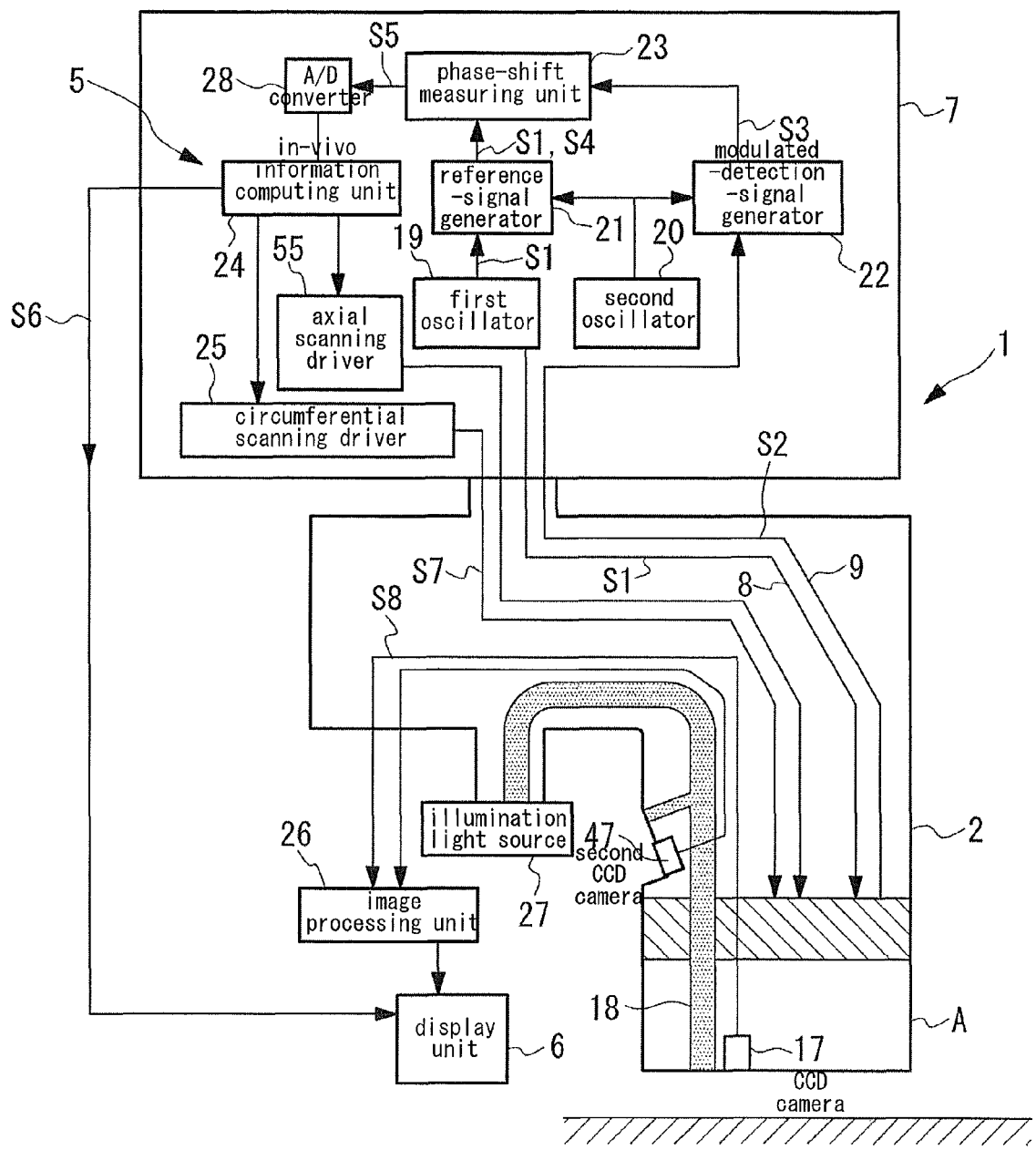
FIG. 16 is an overall schematic diagram showing another modification of the in-vivo information measurement apparatus in FIG. 7.
Figure 17:
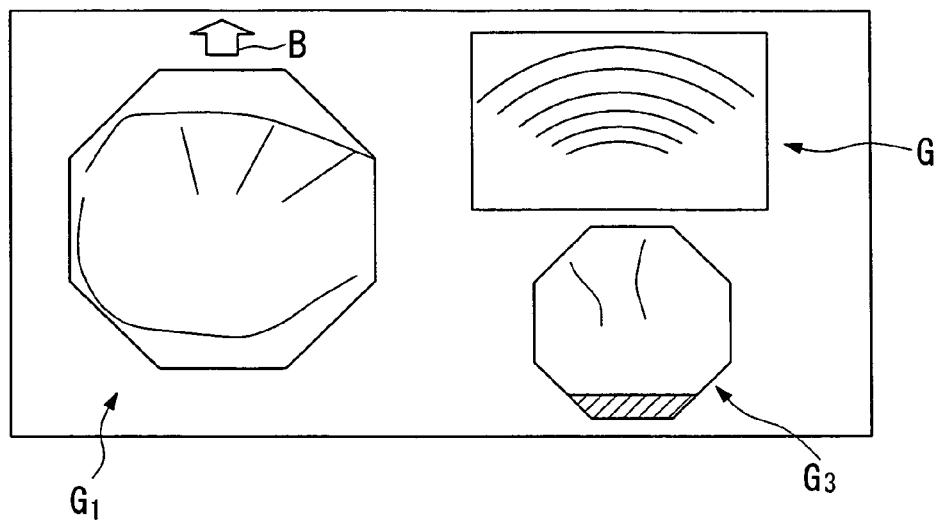
FIG. 17 shows an example of the screen display for a measurement image obtained by the in-vivo information measurement apparatus in FIG. 16.

As shown in FIG. 16, in addition to the CCD camera 17 in the endoscope, a second CCD camera 47 that can acquire the condition of the body cavity surface X in the vicinity of the measurement head unit 2 may also be provided. The second CCD camera 47 is disposed, for example, facing outwards in the radial direction close to the measurement head unit 2 in the outer surface of the endoscope. With this configuration, an infected area for which in-vivo information S6 is to be acquired can be quickly identified, which allows measurement to be carried out rapidly. An image G3 acquired by the second CCD camera 47 may then be displayed on the monitor, as shown in FIG. 17, via an image processing apparatus 26.

Figure 18:
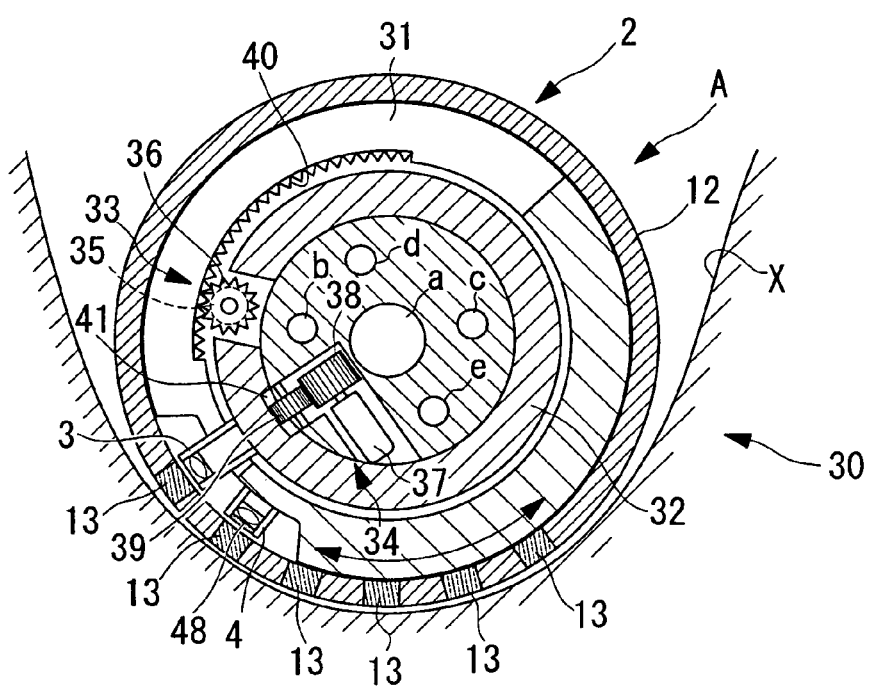
FIG. 18 is a longitudinal section showing another modification of the in-vivo information measurement apparatus in FIG. 7.

As shown in FIG. 18, an excitation-light filter 48 for fluorescence measurement may be disposed in the optical detection unit 4.

For example, by intravenously injecting a fluorescent dye having a characteristic whereby it tends to gather at a specific infected site, such as a cancer, and then carrying out measurement, it is possible to detect fluorescence with the optical detection unit 4 to acquire a fluorescence image. Also, when targeting molecules (enzymes and the like) that commonly occur when cells become cancerous, by intravenously injecting a drug that produces fluorescence when binding (contacting) with that target and thereafter performing fluoroscopy, it is possible to carry out quantitative measurement of the amount of the drug.

Figure 19:
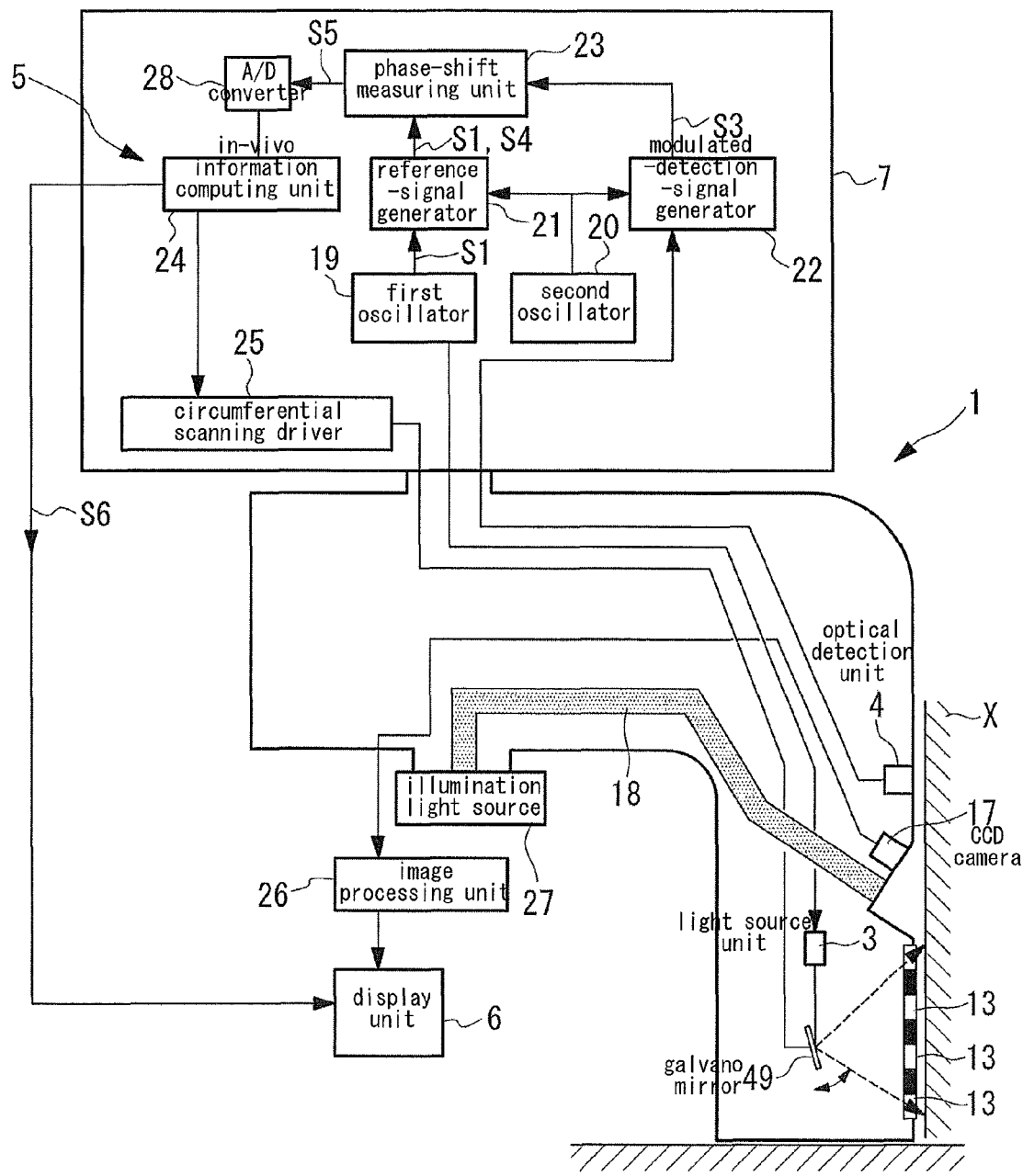
FIG. 19 is an overall schematic diagram showing another modification of the in-vivo information measurement apparatus in FIG. 7.

In addition, in the embodiments described above, the movable members 10, 31, 32, and 46 to which the light source unit 3 and/or the optical detection unit 4 are fixed in the measurement head unit 2 are provided and the measurement region is changed by moving the movable members 10, 31, 32, and 46. Instead of this configuration, however, as shown in FIG. 19, the light from the light source unit 3 may be scanned over a predetermined region of the body cavity surface X by a scanning mechanism, such as a galvano mirror 49, and detected by the optical detection unit 4, which is disposed at a separate position. By providing a plurality of window portions 13 in the irradiation region with a predetermined gap therebetween, for example, a gap of 10 mm, and rotating the two galvano mirrors 49 (only one is shown in the figure) about mutually orthogonal axes, it is possible to irradiate the body cavity surface X with light in both the circumferential direction and the axial direction.

Figure 20:
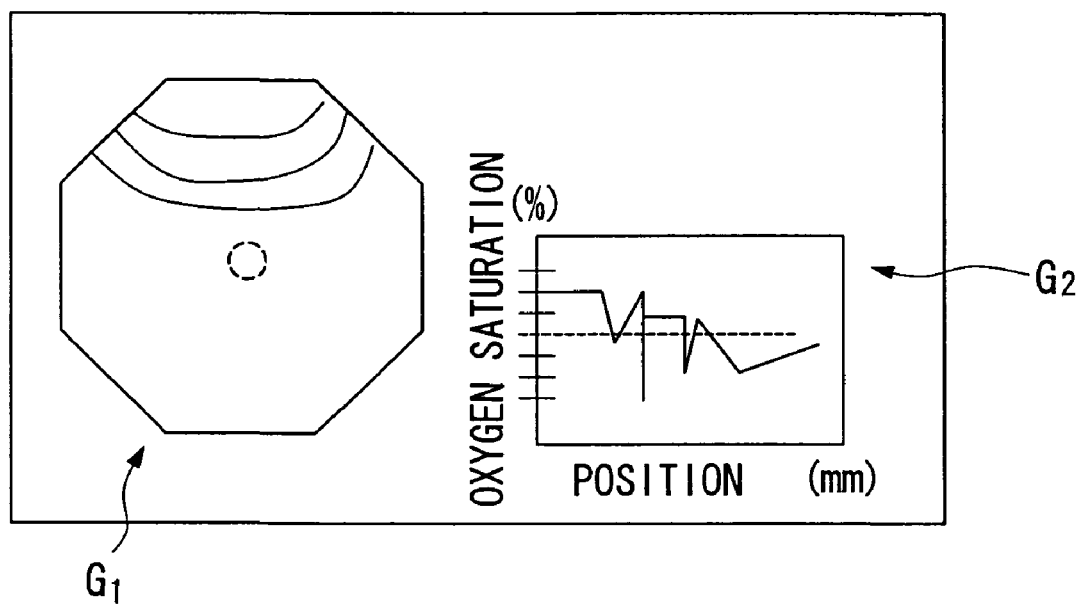
FIG. 20 shows an example of the screen display for a measurement image obtained by the in-vivo information measurement apparatus in FIG. 19.

At this point, as shown in FIG. 19, by arranging the irradiation position and the optical detection unit 4 on either side of the CCD camera 17, it is possible to simultaneously measure the in-vivo information S6 of the tissue at the same depth position while observing the condition of the body cavity surface X. An example of the display shown on the monitor screen in this case is shown in FIG. 20. With this embodiment, the region where the in-vivo information S6 is measured can be indicated in the endoscope image G1.

Figure 21:
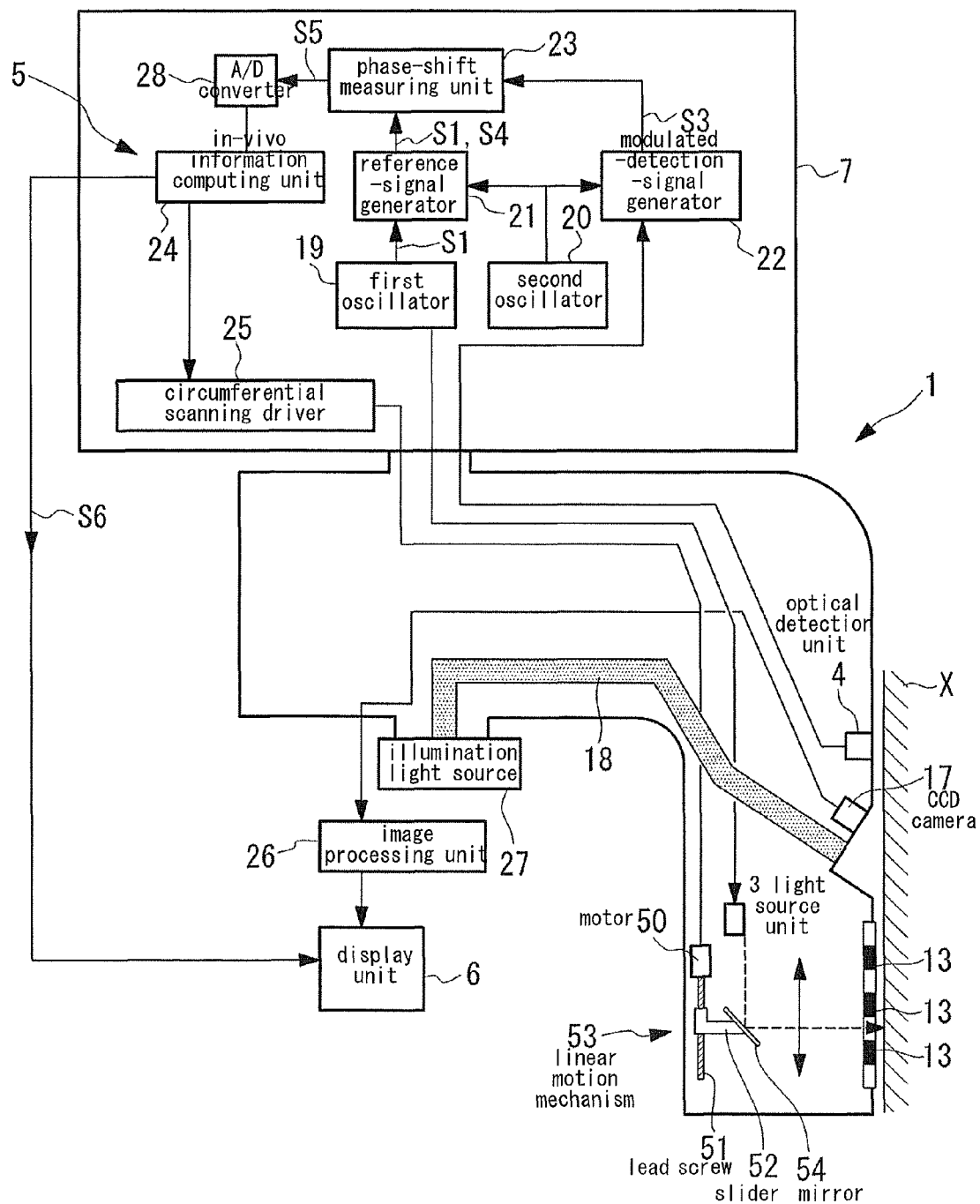
FIG. 21 is an overall schematic diagram showing a modification of the in-vivo information measurement apparatus in FIG. 19.

Instead of the galvano mirrors 49 mentioned above, as shown in FIG. 21, a mirror 54 may be translated by a linear motion mechanism 53 formed of a motor 50, a lead screw 51, and a slider 52 provided inside the endoscope. Instead of the lead screw, the slider 52 may be driven by a gear.

Third Embodiment

An in-vivo information measurement apparatus 61 according to a third embodiment of the present invention will be described below with reference to FIGS. 22 to 26.

Figure 22:
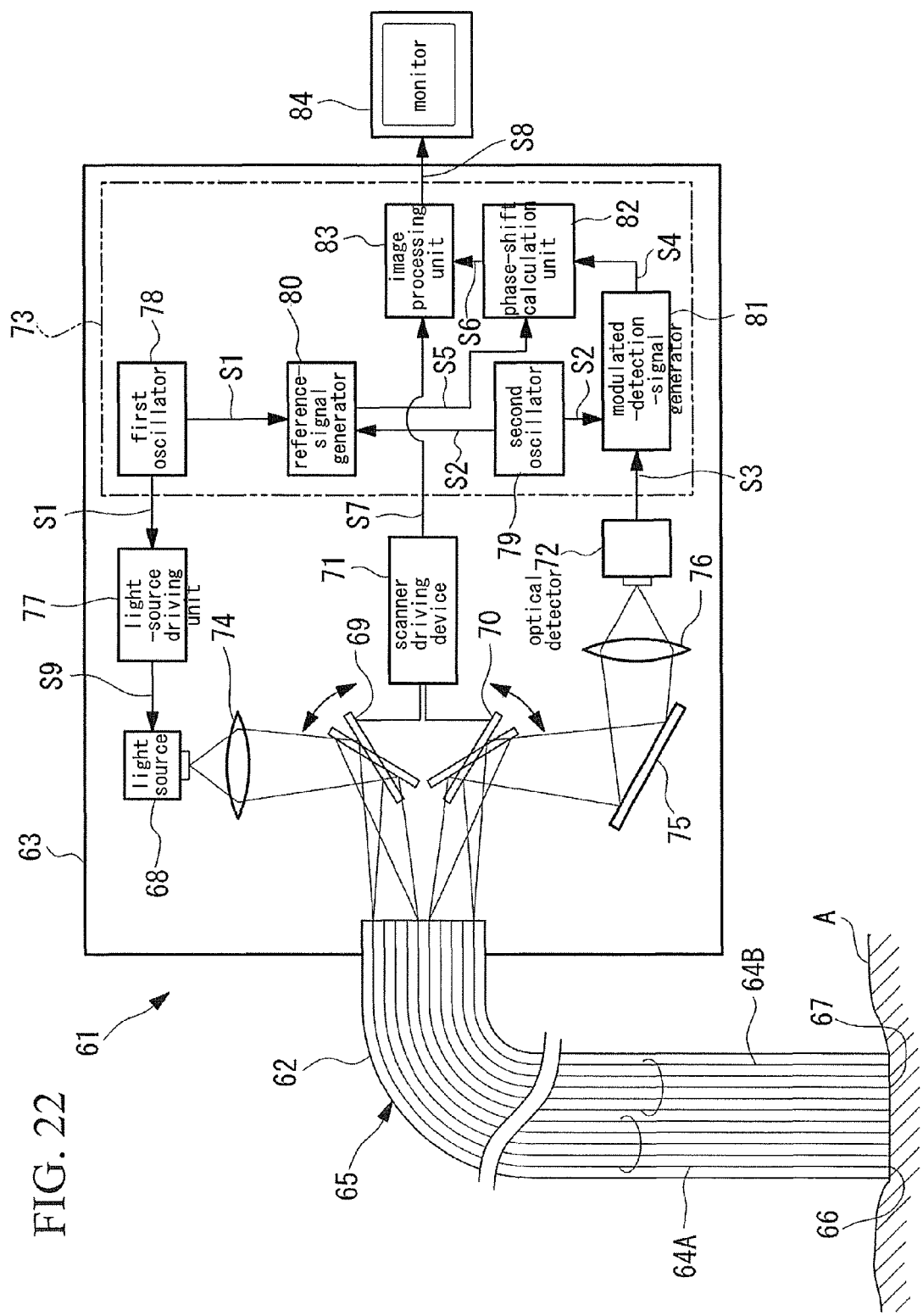
FIG. 22 is an overall schematic diagram showing an in-vivo information measurement apparatus according to a third embodiment of the present invention.

The in-vivo information measurement apparatus 61 according to this embodiment mainly performs examination of an examination site in a body cavity by inserting it into the body cavity, and as shown in FIG. 22, includes a probe 62 that is inserted into the body cavity and an apparatus main body 63 that is connected to the probe 62 and disposed outside the body cavity.

The probe 62 includes an optical fiber bundle 65 formed of a plurality of optical fibers 64A and 64B. Ends of the optical fibers 64A and 64B are disposed so as to be exposed at one end of the probe 62 positioned inside the body cavity. The optical fiber bundle 65 is divided into two groups of optical fibers, namely, the optical fibers 64A and 64B; the ends of one of the groups of fibers, that is, the optical fibers 64A, constitute light projection units 66, and the ends of the other group, that is, the optical fibers 64B, constitute light receiving units 67.

The apparatus main body 63 includes a light source 68; a first scanning mirror 69 that two-dimensionally scans the light emitted from the light source 68 and introduces it to the other ends of the optical fibers 64A, which have the light projecting units 66 at one end thereof; a second scanning mirror 70 that two-dimensionally scans return light received by the light receiving units 67 and transmitted through the optical fibers 64B; a scanner driving device 71 for driving the scanning mirrors 69 and 70; an optical detector 72 that detects the return light scanned by the second scanning mirror 70; and a signal processing unit 73. In this figure, reference numeral 74 represents a focusing lens that focuses light emitted from the light source 68, reference numeral 75 represents a fixed mirror that deflects the light scanned by the second scanning mirror 70, and reference numeral 76 represents a focusing lens that focuses the return light deflected by the fixed mirror 75 onto the optical detector 72. In addition, reference numeral 84 indicates a monitor.

The light source 68 is formed, for example, of a laser diode (LD), which emits laser light of a frequency specified by a light-source driving unit (light modulator) 77. The optical detector 72 is, for example, a photodiode (PD).

Among the two groups of optical fibers 64A and 64B, all of the ends of the optical fibers 64A are disposed within the scanning range of the first scanning mirror 69 so as to make the light from the light source 68 incident on one of the groups of fibers, namely, the optical fibers 64A.

The second scanning mirror 70 is oscillated so that the return light issuing from the ends of all of the optical fibers 64B in the other group is directed towards the optical detector 72.

The signal processing unit 73 includes a first oscillator 78, a second oscillator 79, a reference-signal generator 80, a modulated-detection-signal generator 81, a phase-shift calculation unit 82, and an image processing unit 83.

The first oscillator oscillates a first-frequency signal S1 having a first frequency of, for example, 200 MHz. The first-frequency signal S1 that is oscillated is input to the light-source driving unit 77 so as to cause the light source 68 to emit intensity-modulated light that is modulated at the first frequency. The first-frequency signal S1 from the first oscillator 78 is also input to the reference-signal generator 80.

The second oscillator 79 oscillates a second-frequency signal S2 having a second frequency of, for example, 200.05 MHz. The second-frequency signal S2 that is oscillated is input to the modulated-detection-signal generator 81. The modulated-detection-signal generator 81 subjects a detection signal S3 detected by the optical detector 72 to modulation at the second frequency oscillated by the second oscillator 79 to produce a modulated detection signal S4. The second-frequency signal S2 from the second modulator 79 is also input to the reference-signal generator 80.

The reference signal generator 80 generates a reference signal S5 having a difference frequency equal to the difference between the first-frequency signal S1 input from the first oscillator 78 and the second-frequency signal S2 input from the second oscillator 79. The phase-shift calculation unit 82 calculates a phase-shift signal S6 between the modulated detection signal S4, which is detected by the optical detector 72 and modulated at the second frequency, and the reference signal S5 input from the reference-signal generator 80. The image processing unit 83 calculates in-vivo information based on the phase-shift signal S6.

The in-vivo information is, for example, the oxygen concentration, hemoglobin concentration, water content, carbon dioxide concentration, absorption coefficient, scattering coefficient, and so forth in biological tissue.

The scanner driving device 71 changes the angles of the first and second scanning mirrors 69 and 70 and outputs to the image processing unit 83 position information S7 of the light projection unit 66 and the light receiving unit 67 determined by those angles. Then, the image processing unit 83 generates an image signal S8 based on the in-vivo information calculated as described above and the position information S7 of the light projection unit 66 and the light receiving unit 67 input from the scanner driving device 71.

Figure 23A:
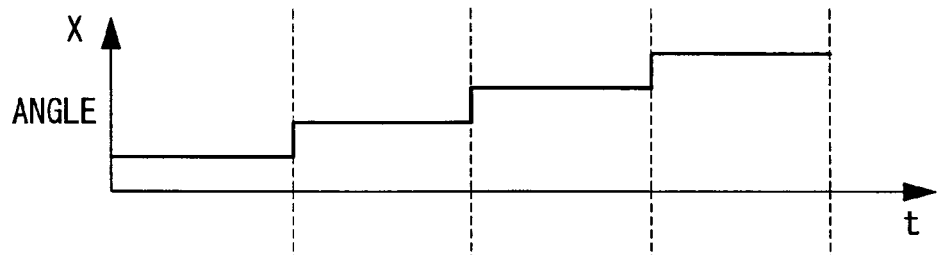
FIGS. 23A and 23B are timing charts showing examples of operating patterns of a scanning mirror in the in-vivo information measurement apparatus in FIG. 22.
Figure 23B:
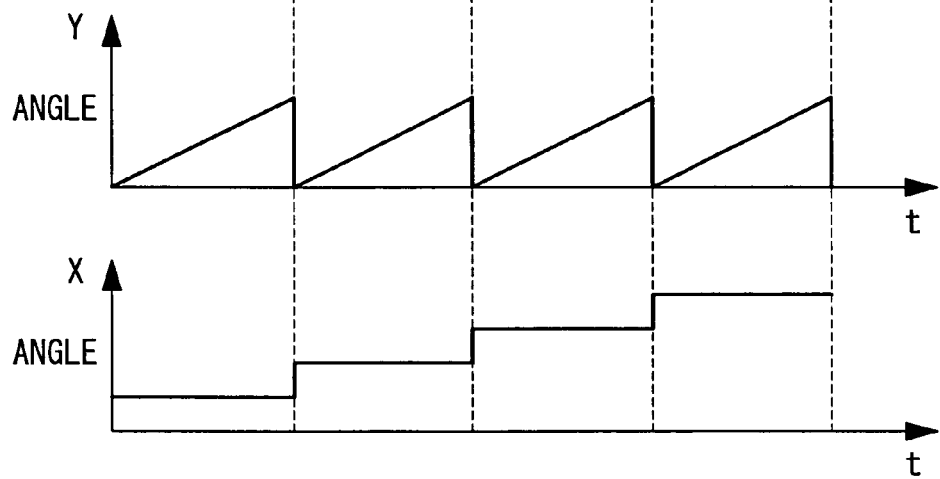

Examples of the driving patterns of the first and second scanning mirrors 69 and 70 produced by the scanner driving device 71 are shown in FIGS. 23A and 23B. More specifically, as shown in FIG. 23A, the angle of first scanning mirror 69 is varied one-dimensionally in a step-like manner with a fixed period. On the other hand, in synchronization with the operation of the first scanning mirror 69, the angle of the second scanning mirror 70 is varied in a step-like manner in one direction while varying it in a saw-tooth manner in the direction orthogonal thereto, as shown in FIG. 23B. In other words, the second scanning mirror 70 is moved two-dimensionally.

Figure 24:
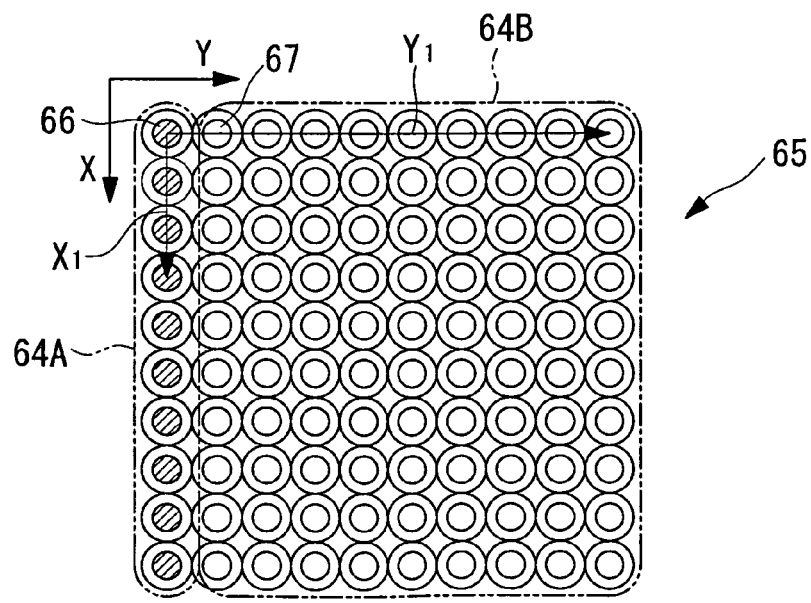
FIG. 24 is a diagram for explaining the operating patterns of a light projection unit and a light receiving unit according to the timing charts in FIGS. 23A and 23B.

By driving the first and second scanning mirrors 69 and 70 in this way, the light projection units 66 and the light receiving units 67 change as shown in FIG. 24. More specifically, by one-dimensionally varying the angle of the first scanning mirror 69, the position of the selected light projection unit 66 changes in the X-direction, as indicated by the arrow X1. Likewise, regarding the position of the selected light receiving unit 67, the ends of the optical fibers 64B aligned in a row in the Y direction corresponding to the light projection unit 66 that emits light are sequentially selected as the light receiving units 67 in the Y direction, as indicated by the arrow Y1, by varying the angle of the second scanning mirror 70 in the first period. Then, in the second period, after moving one row in the X direction, the light receiving units 67 are again sequentially selected in the Y direction.

The operation of the in-vivo information measurement apparatus 61 according to this embodiment, having such a configuration, will be described below.

To measure in-vivo information using the in-vivo information measurement apparatus 61 according to this embodiment, the probe 62 is inserted into the body cavity, and the light projection units 66 and the light receiving units 67 disposed at the tip of the probe 62 are brought into contact with the vicinity of an infected area on a surface A inside the body cavity.

Then, the scanner driving device 71 is operated, and when the first and second scanning mirrors 69 and 70 are set at predetermined angles, the light source unit 68 is activated. Since a driving command signal S9 according to the first-frequency signal S1 produced by the first oscillator 78 is input to the light source 68 from the light-source driving unit 77, intensity modulated light that is modulated at the first frequency is emitted from the light source 68.

The intensity modulated light is focused by the focusing lens 74 onto the end of a predetermined optical fiber 64A selected from the fibers in the optical fiber bundle 65 by the first scanning mirror 69. Thus, the other end of the optical fiber 64A on which the intensity modulated light is focused, in other words, the end in contact with the body cavity surface A, serves as the light projection unit 66, and the intensity modulated light is irradiated towards the interior from the body cavity surface A.

At this point, the second scanning mirror 70 is set at an angle at which the return light transmitted by the optical fiber 64B whose end is adjacent to the light projection unit 66 in the Y-direction is incident on the optical detector 72. Therefore, as shown in FIG. 24, the end of the optical fiber 64B adjacent to the light projection unit 66 in the Y-direction serves as the light receiving unit 67.

In this state, the return light falling on the light receiving unit 67 propagates through the optical fiber 64B to return to the interior of the apparatus main body 63 and is made incident on the optical detector 72 via the second scanning mirror 70, the fixed mirror 75, and the focusing lens 76, to produce the detection signal S3 with the optical detector 72.

When the detection signal S3 is input to the signal processing unit 73, it forms the modulated detection signal S4 after being modulated by the second-frequency signal S2 output from the second oscillator 79, which is then input to the phase-shift calculating unit 82. In the phase-shift calculating unit 82, the phase-shift S6 is calculated based on the input modulated detection signal S4 and the reference signal S5 whose frequency is equal to the difference between the first and second frequencies; the phase-shift S6 is then input to the image processing unit 83. In-vivo information, such as the oxygen concentration, hemoglobin concentration, water content, carbon dioxide concentration, absorption coefficient, scattering coefficient, or the like, is computed in the image processing unit 83 based on the phase shift S6.

Since the position information S7 of the light projection unit 66 and the light receiving unit 67 set by the scanner driving device 71 is input to the image processing unit 83, it is possible to ascertain the position on the body cavity surface A to which the computed in-vivo information corresponds. Therefore, an image displaying the relationship between the in-vivo information and the position information S7 of the light projection unit 66 and the light receiving unit 67 is displayed on the monitor 84.

Next, based on the operation of the scanner driving device 71, the angle of the second scanning mirror 70 is varied so as to sequentially move to the next light receiving unit 67 in the Y-direction. Thus, the position of the light receiving unit 67 is sequentially changed in the Y direction while keeping the position of the light projection unit 66 fixed, and measurement of the in-vivo information is carried out each time.

When motion along one complete row of light receiving units 67 by the second scanning mirror 70 is completed, the angles of the first scanning mirror 69 and the second scanning mirror 70 are adjusted so as to shift the light projection unit 66 and the light receiving unit 67 by one row in the X-direction. The angle of the second scanning mirror 70 is then changed again so as to set the light receiving unit 67 at the end of the optical fiber 64B adjacent to the light projection unit 66 newly set by the first scanning mirror 69. Thereafter, by changing the angle of the second scanning mirror 70 in the same way as described above, it is possible to sequentially move the position of the light receiving unit 67 in the Y-direction. In the same way as described below, by repeating the above-described operation up to a predetermined position in the X-direction, measurement of the in-vivo information is carried out over a predetermined range in the X-direction.

Figure 25:
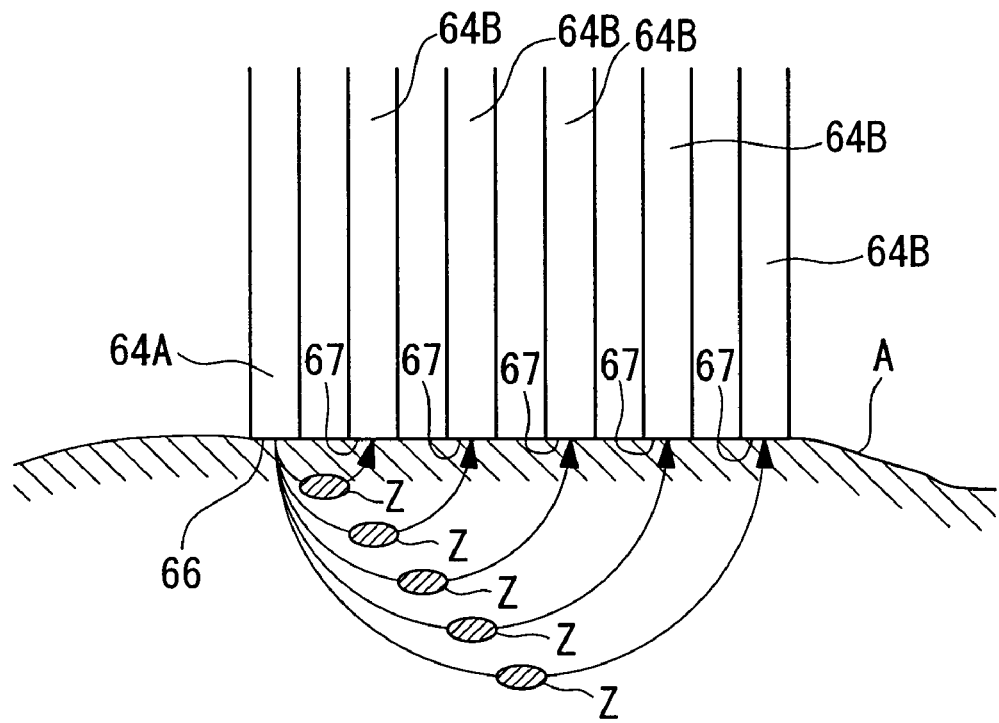
FIG. 25 is a diagram schematically showing a light path inside a body from the light projection unit to the light receiving unit in the case where measurement is performed according to the timing charts in FIGS. 23A and 23B.
Figure 26:
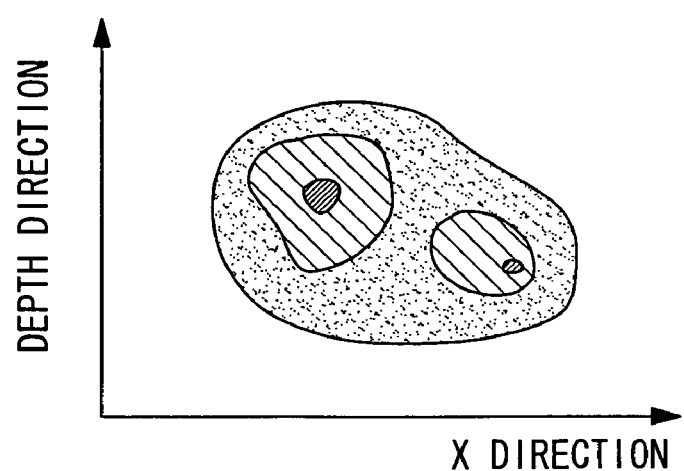
FIG. 26 is a diagram showing the distribution of in-vivo information measured according to the operating patterns in FIG. 24.

In such a case, according to this embodiment, the intensity modulated light is emitted from a fixed light projection unit 66 for each row in the X-direction, and the distance between the light projection unit 66 and the light receiving unit 67 changes because the light receiving unit 67 that receives return light from the body sequentially moves in the Y-direction. The intensity modulated light introduced into the body returns to the body cavity surface A due to diffusion or transmission in the body. In general, however, as shown in FIG. 25, it is known that the light penetrates to a position Z at a depth determined by the distance between the light projection unit 66 and the light receiving unit 67. In other words, when the distance between the light projection unit 66 and the light receiving unit 67 is small, the light penetrates to a relatively shallow position, and as the distance therebetween becomes larger, the light penetrates to deeper positions. Therefore, according to this embodiment, for each row in the X direction, it is possible to measure the distribution of in-vivo information in the depth direction of the body. With the in-vivo information measurement apparatus 61 according to this embodiment, the image obtained by the image processing unit 83 shows a two-dimensional distribution of in-vivo information in the X-direction and the depth direction, as shown in FIG. 26.

Hence, with the in-vivo information measurement apparatus 61 according to this embodiment, it is possible to measure the in-vivo information over a wide area within a short period of time simply by varying the angle of the first and second scanning mirrors 69 and 70, and it is possible to perform two-dimensional imaging of the in-vivo information.

Although the optical fiber bundle 65 formed of the plurality of optical fibers 64A and 64B is disposed inside the probe 62 in this embodiment, instead of this configuration, the optical fiber bundle 65 may be formed of a fiber bundle having a plurality of optical fiber cores. By doing so, it is possible to increase the optical fiber core density, which enables the resolution to be improved.

Figure 27:
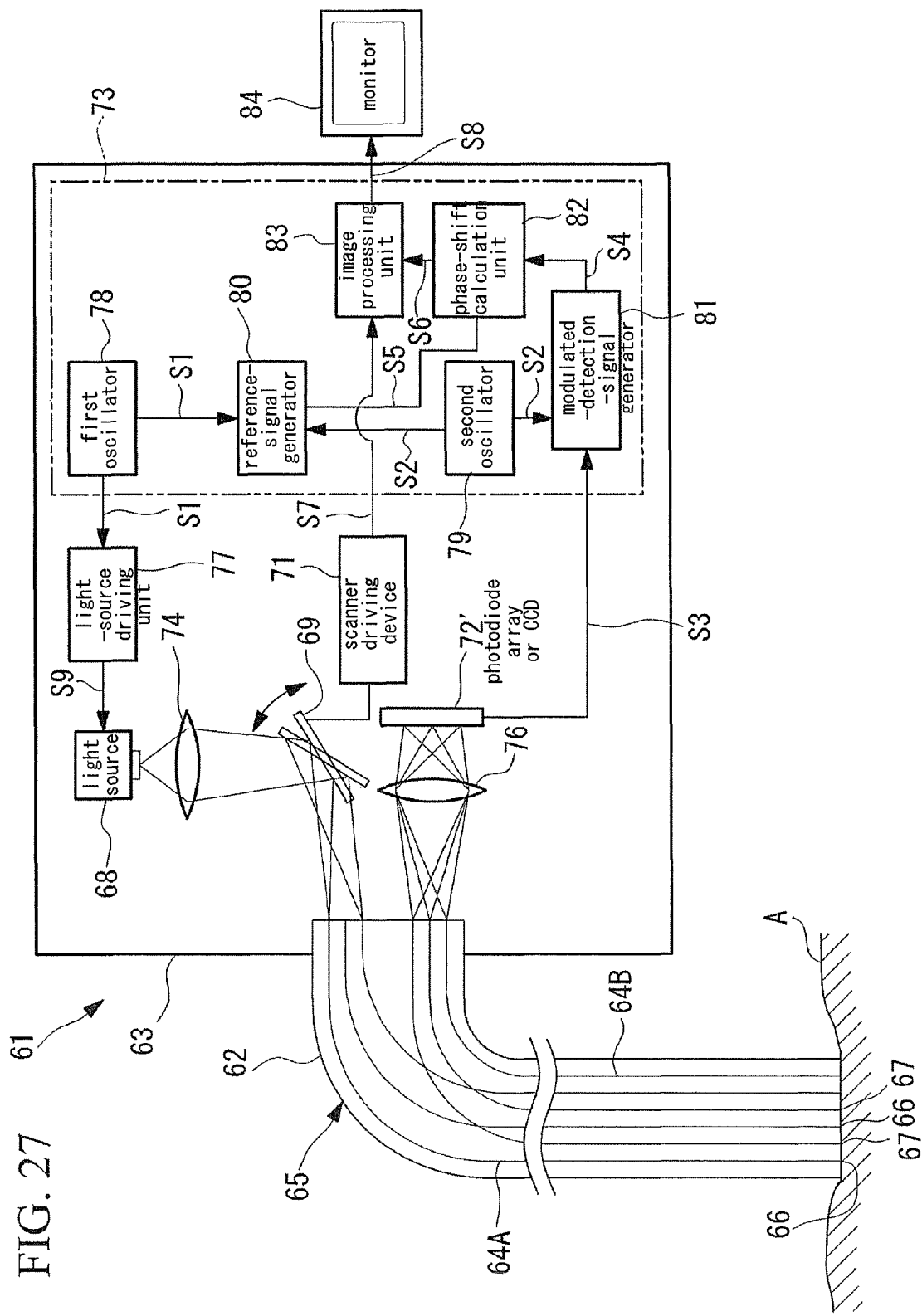
FIG. 27 is an overall schematic diagram showing a first modification of the in-vivo information measurement apparatus in FIG. 22.

Furthermore, although a photodiode is used as the optical detector 72 in the present embodiment, instead of this, a photodiode array or CCD 72' that is capable of acquiring two-dimensional images may be used, as shown in FIG. 27. By doing so, the second scanning mirror 70 becomes unnecessary.

Figure 28:
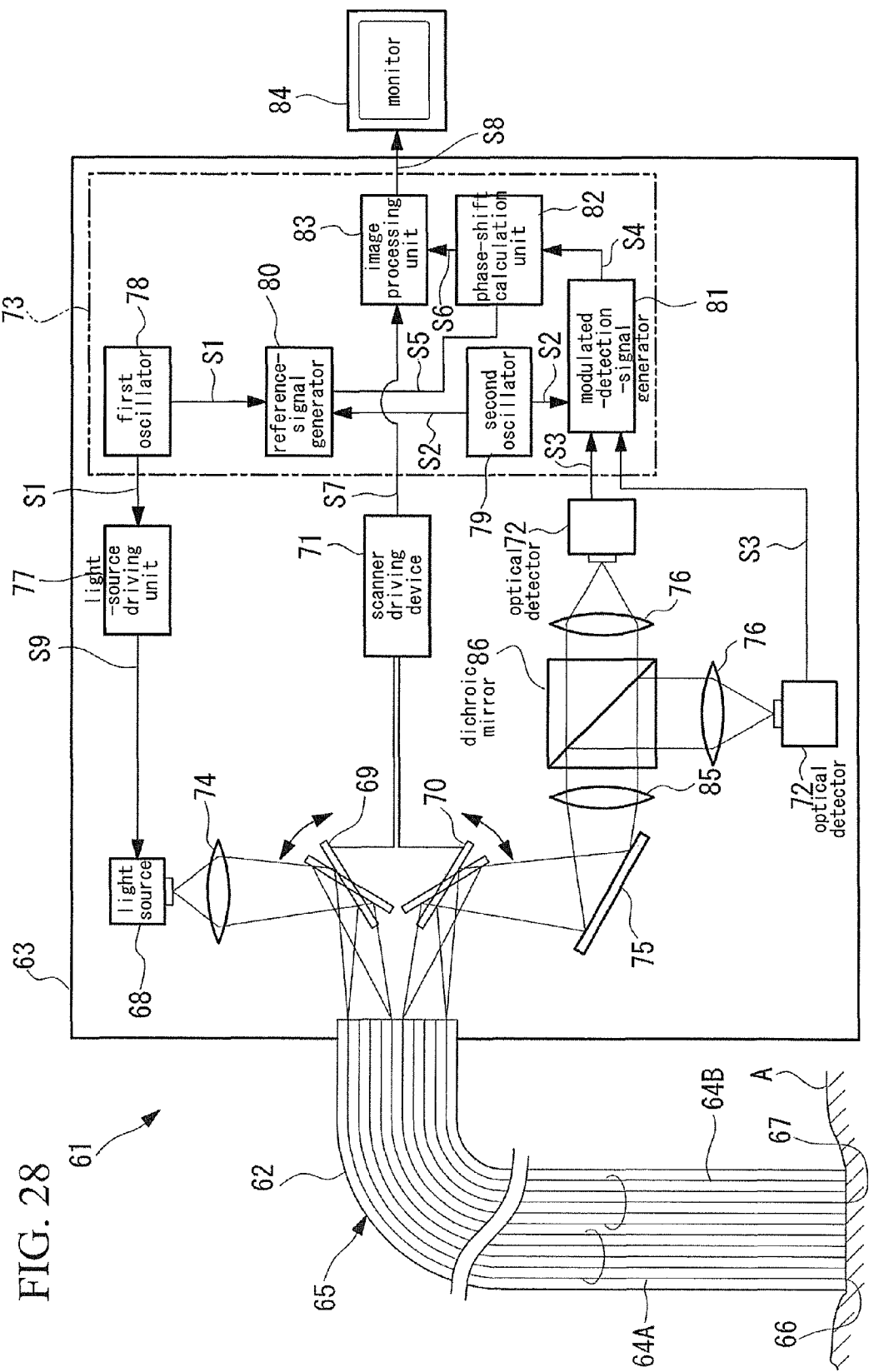
FIG. 28 is an overall schematic diagram showing a second modification of the in-vivo information measurement apparatus in FIG. 22.

In addition, as shown in FIG. 28, a laser diode that is capable of selectively emitting laser light having a plurality of wavelengths using a wavelength selection mechanism (not shown) may be employed as the light source 68. In this case, a plurality of photodiodes 72 that can respectively detect the plurality of different wavelengths may be provided, and a collimator lens 85 and a dichroic mirror 86 that transmits or reflects the return light depending on the wavelength of the return light incident thereon may be provided between the fixed mirror 75 and the photodiodes 72.

Figure 29A:
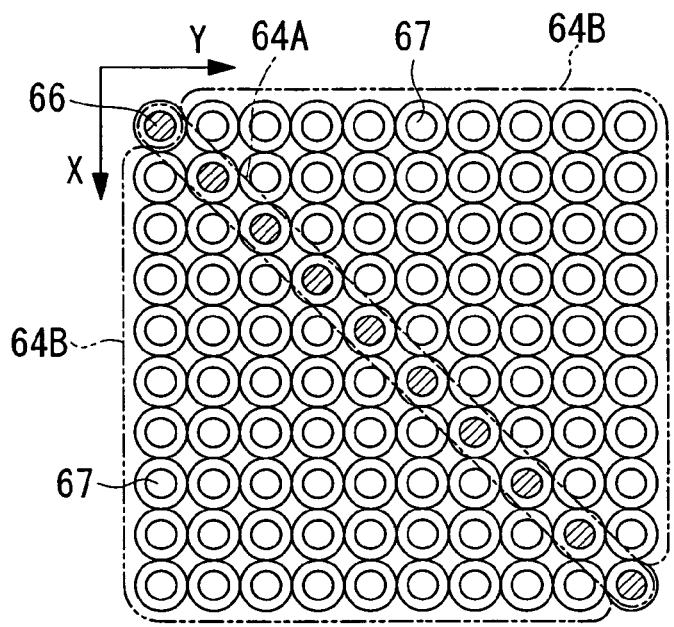
FIGS. 29A and 29B are diagrams for explaining other operating patterns of the light projection unit and the light receiving unit.
Figure 29B:
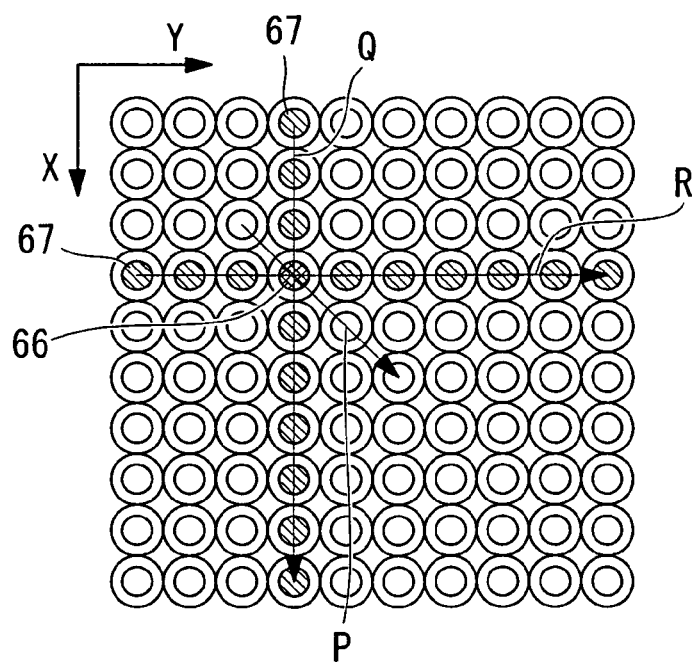

The light projection units 66 shown in FIGS. 27 and 28 may be disposed such that the light projection units 66 located at the tip of the probe 62 are distributed in the Y direction as well as in the X-direction, as shown in FIGS. 29A and 29B. In such a case, as shown in FIG. 29A, by disposing the optical fibers 64A serving as the light projection units 66 at an angle with respect to the X and Y directions and operating the first scanning mirror 69, the sequential motion of the light projection units 66 is in the direction of the arrow P, as shown in FIG.

Figure 30:
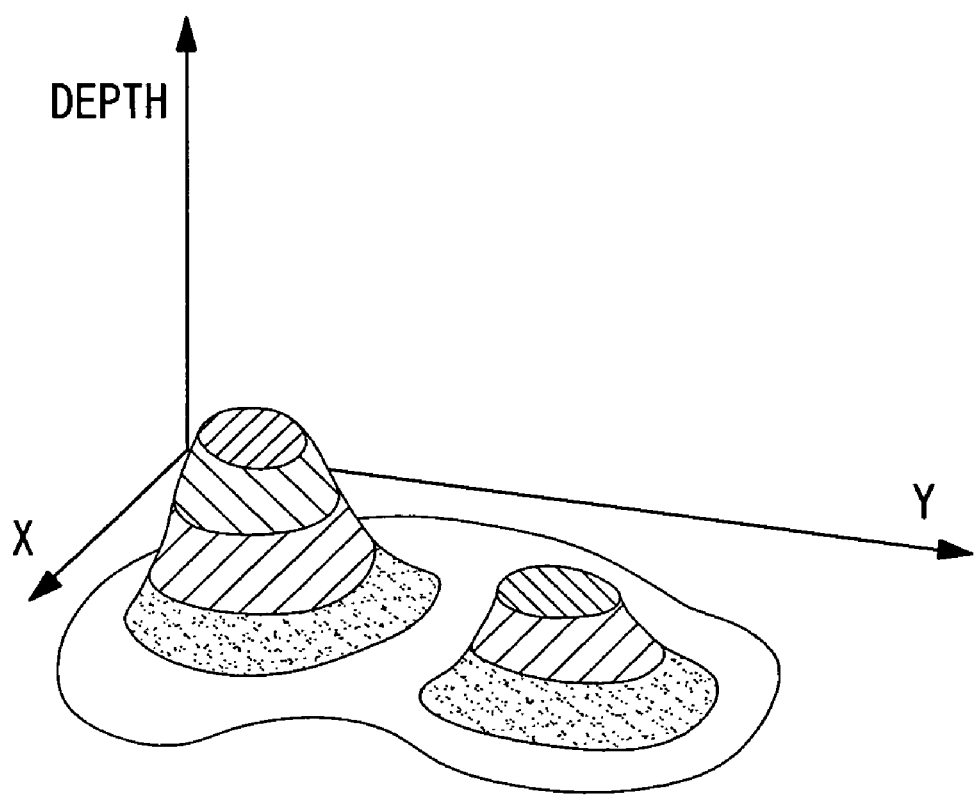
FIG. 30 is a diagram showing the distribution of in-vivo information measured according to the operating patterns in FIGS. 29A and 29B.

29B. Then, the selection of the light receiving units 67 by the second scanning mirror 70 is carried out sequentially for the optical fibers 64B arrayed along the row and column in the X-direction and the Y-direction that include each light projection unit 66, as shown by arrows Q and R. With this configuration, since the distribution of the in-vivo information can be acquired not only in the X-direction but also in the Y-direction, it is possible to acquire the distribution of in-vivo information in the X and Y directions and in the depth direction, as shown in FIG. 30. In such a case, it possible to display the density of the in-vivo information by varying the image color according to the density.

Figure 31:
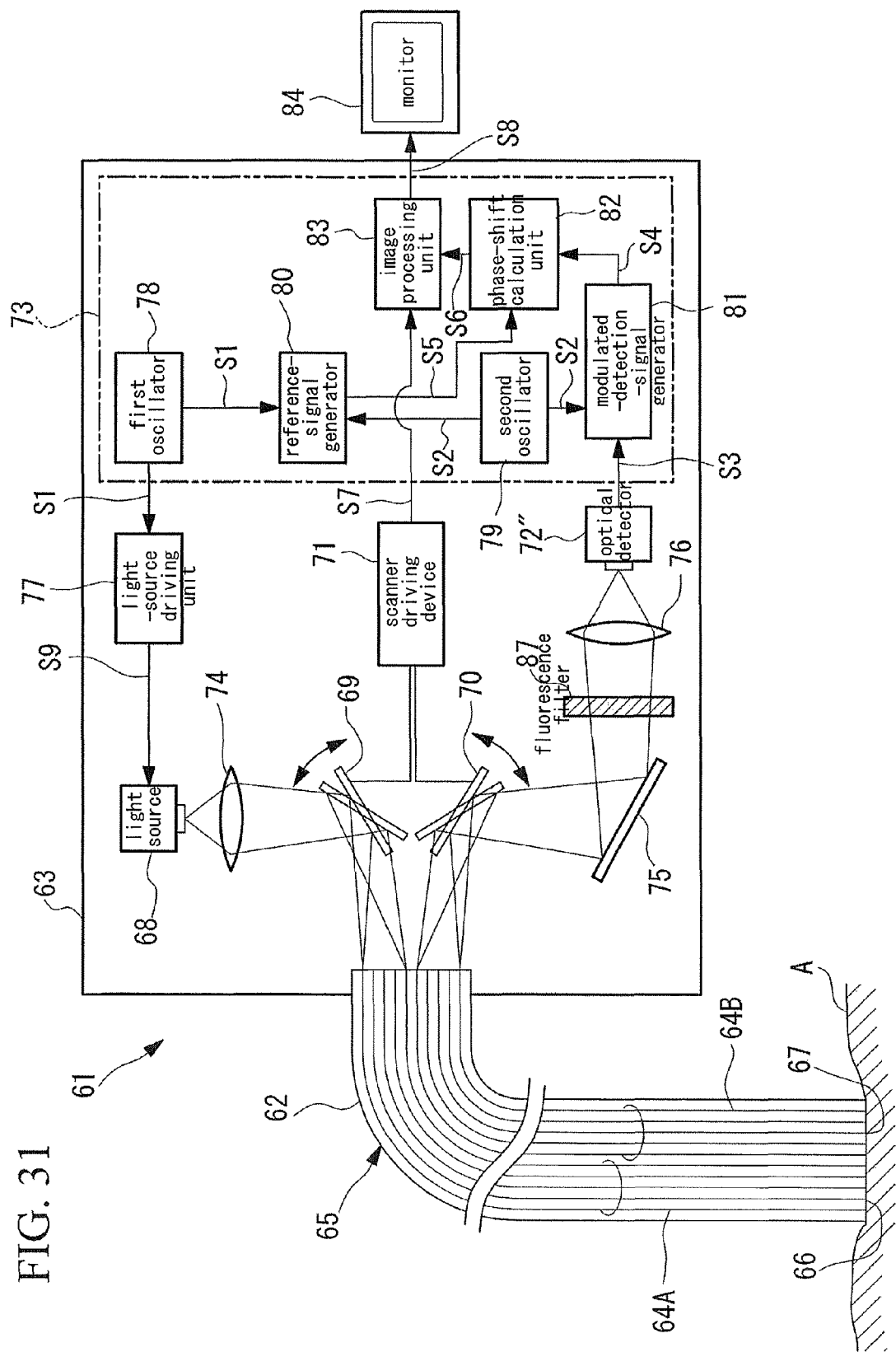
FIG. 31 is an overall schematic diagram showing a third modification of the in-vivo information measurement apparatus in FIG. 22.

In the in-vivo information measurement apparatus 61 according to this embodiment, when the return light from the body being observed is fluorescence, a photomultiplier tube (PMT), with a fluorescence filter 87 placed in front, is employed as an optical detector 72″, as shown in FIG. 31.

With this arrangement, since light other than the desired fluorescence, for example, laser light reflected at the body cavity surface A, is removed by the fluorescence filter 87, it is possible to efficiently detect only fluorescence with the optical detector 72″.

Figure 32:
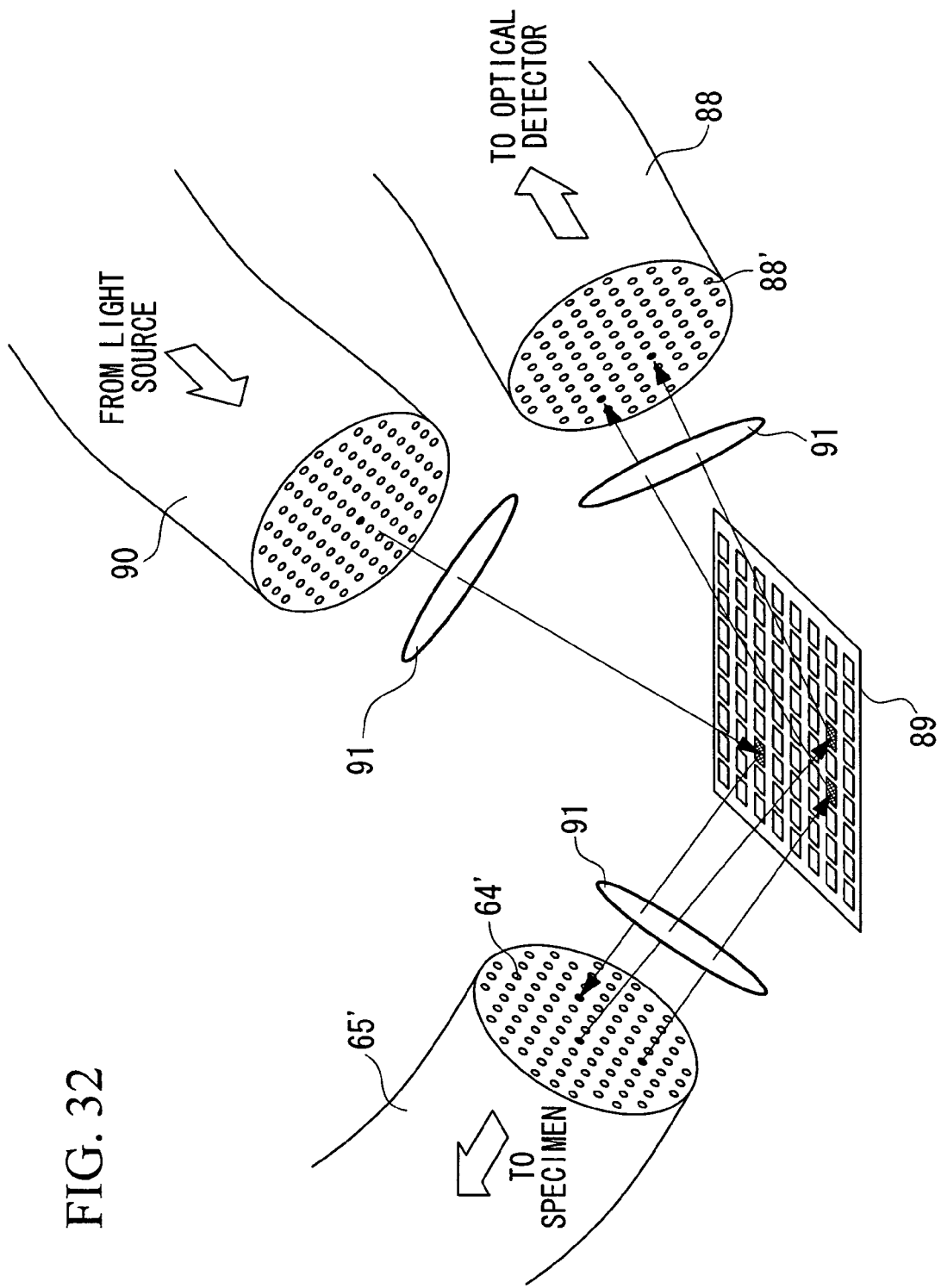
FIG. 32 is a diagram showing a fourth modification of the in-vivo information measurement apparatus in FIG. 22.

In the in-vivo information measurement apparatus 61 according to the embodiment described above, the optical fiber bundle 65 in the probe 62 is divided into two groups, one being for light projection and the other being for light reception; however, it is also possible for all optical fibers (optical fiber cores) 64 to be commonly used for both light projection and light reception. For example, as shown in FIG. 32, the emitted light is incident on a desired optical fiber core 64′ of an optical fiber bundle 65′ to select any light projection unit 66, and a MEMS mirror array 89 in which light received by any light reception unit 67 is made incident on an optical fiber core 88′ of a fiber bundle 88 that faces the optical detector 72 is employed. This MEMS mirror array 89 can be used to select all of the optical fiber cores (optical fibers) 64′ for both light projection and light reception. In addition, a plurality of light projection units 66 are formed at once, which affords an advantage in that it is possible to reduce the measurement time. In the figure, reference numeral 90 represents a fiber bundle that guides light from the light source, and reference numeral 91 represents a focusing lens.

Figure 33:
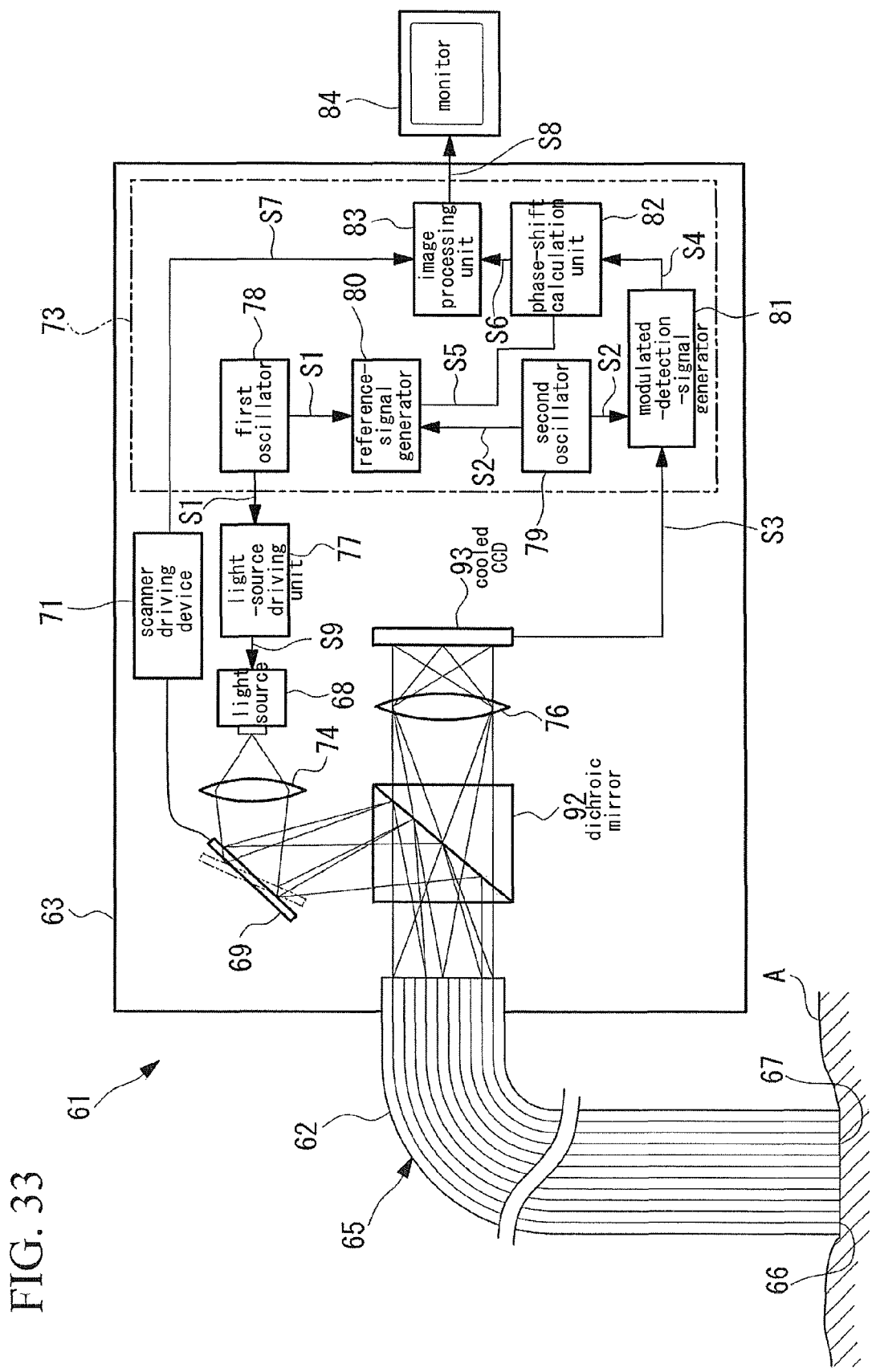
FIG. 33 is an overall schematic diagram showing a fifth modification of the in-vivo information measurement apparatus in FIG. 22.

As shown in FIG. 33, a dichroic mirror 92 may be placed opposite the end of the optical fiber bundle 65 inside the probe 62. In this case, the laser light scanned by the scanning mirror 69 is reflected by the dichroic mirror 92 to be introduced into the optical fiber bundle 65, and fluorescence returning from the optical fiber bundle 65 is transmitted through the dichroic mirror 92 and is incident on a cooled CCD 93. With this arrangement, all fiber cores constituting the optical fiber bundle 65 can be selected for both light projection and light reception, and fluoroscopy can be realized. Also, if a half-mirror is used instead of the dichroic mirror 92, it is possible to realize diffuse-light observation.

Figure 34:
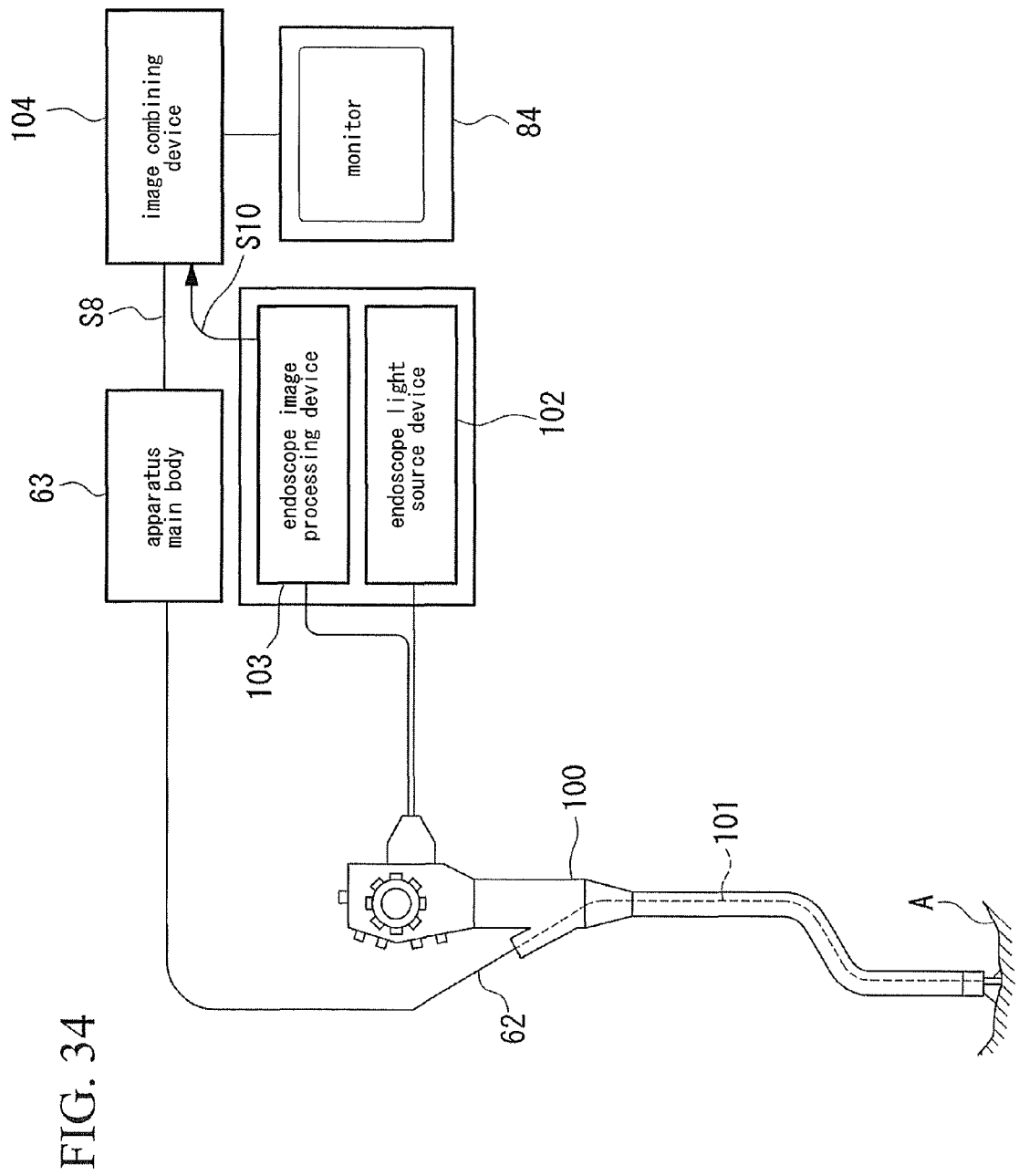
FIG. 34 is an overall schematic diagram showing an example application in the case where a probe of the in-vivo information measurement apparatus in FIG. 22 is inserted into a channel of an endoscope.

In the embodiment described above, a case in which the probe 62 is directly inserted into the body cavity has been described. Instead of this, however, as shown in FIG. 34, the probe 62 may be inserted into a channel 101 in an endoscope 100 for observing a surface A in the body cavity. In this case an image acquired with the endoscope 100 using illumination emitted from an endoscope light source device 102 is subjected to image processing in an endoscope image processing device 103 to output an endoscope image signal S10.

Consequently, an image combining device 104 may be provided for superimposing the endoscope image signal S10 with the image signal S8 output from the apparatus main body 63 of the in-vivo information measurement apparatus 61 according to this embodiment and outputting the result to the monitor 84. With this configuration, the endoscope image of the surface A inside the body cavity and the in-vivo information of the interior of the body in the vicinity thereof can be associated with each other and confirmed at a glance.

In this case, it is preferable to expose the tip of the probe 62, which is inserted into the channel 101, from the tip of the endoscope 100, and to dispose a portion thereof within the field of view of the endoscope 100. By doing so, it is possible to confirm the measurement position of the in-vivo information by means of the endoscope image.

Figure 35:
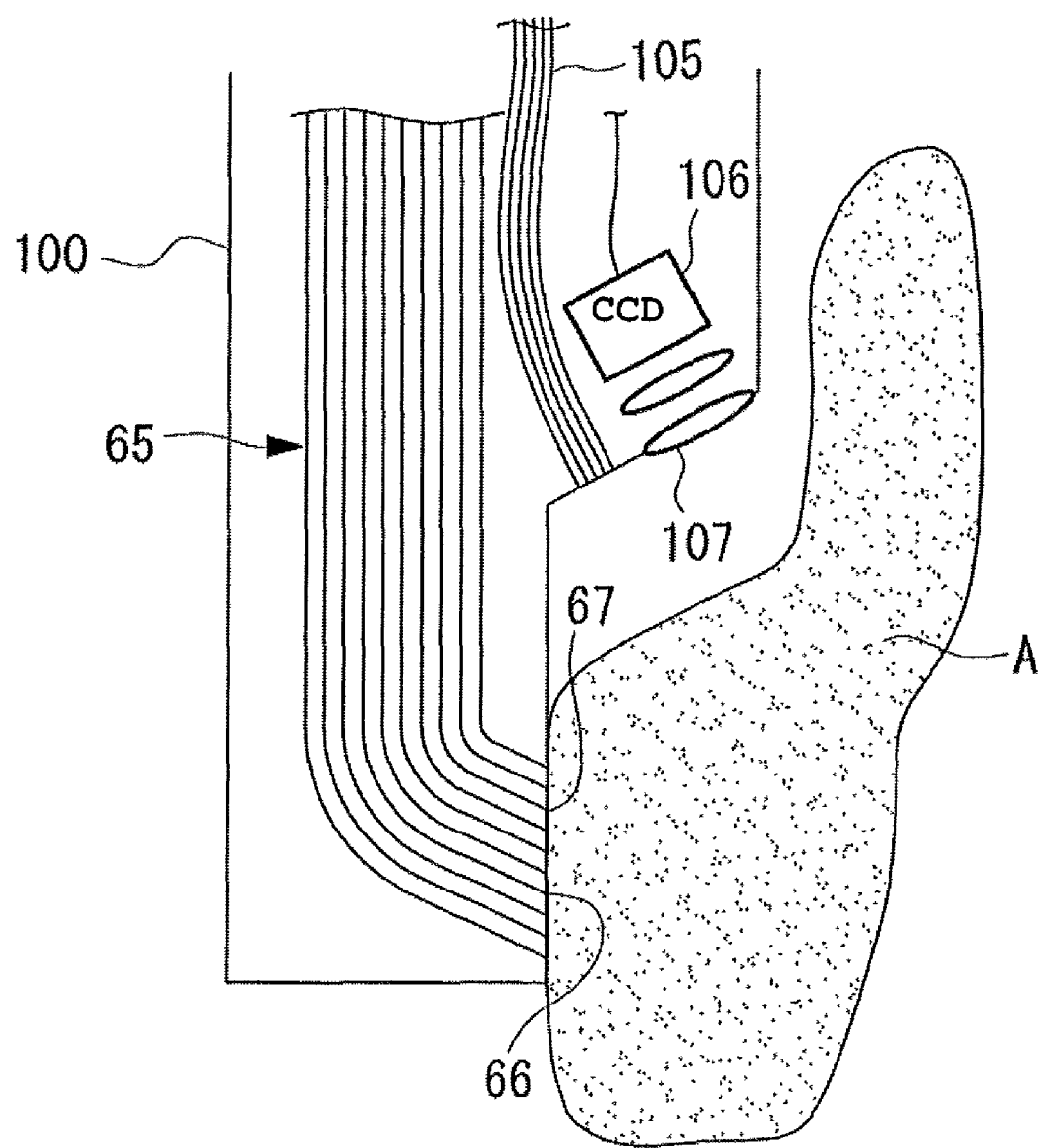
FIG. 35 is a schematic longitudinal section of the tip of the endoscope, in which the probe is fixed inside the endoscope.

Instead of inserting the probe 62 into the channel 101 of the endoscope 100, the optical fiber bundle 65 may be fixed inside the endoscope 100, as shown in FIG. 35. Reference numeral 105 in the drawing represents a light guide that transmits illumination light from the light source device 102, reference numeral 106 represents a CCD that acquires endoscope images, and reference numeral 107 represents an objective lens. In this case too, since a portion at the location of the tip of the probe 62 is disposed within the field of view of the endoscope 100, it is possible to confirm the measurement position of the in-vivo information by means of the endoscope image.

What is claimed is:

1. An in-vivo information measurement apparatus comprising:
   an insertion part for insertion into a body cavity;
   a tubular cover member disposed at the outermost periphery of the insertion part;
   a plurality of transparent window portions disposed with gaps therebetween on the cover member;
   a light projection unit, provided at a tip of the insertion part, that irradiates an examination site inside the body cavity via the window portion with intensity-modulated light intensity modulated at a first frequency;
   a light receiving unit, provided at the tip of the insertion part, that receives return light from the examination site via the window portion at a different position from the light projection unit;
   an optical detector that detects return light from the examination site received at the light receiving unit;
   an in-vivo information calculation unit that calculates in-vivo information for the examination site based on a phase shift between a modulated detection signal, formed by modulating a detection signal from the optical detector at a second frequency, and a reference signal having a difference frequency equal to the difference between the first frequency and the second frequency; and
   moving mechanism that moves at least one of the light projection unit and the light receiving unit in a disposition direction of the plurality of transparent window portions.

2. An in-vivo information measurement apparatus according to claim 1, wherein the insertion part is an endoscope.

3. An in-vivo information measurement apparatus according to claim 1, wherein the insertion part is an elongated probe.

4. An in-vivo information measurement apparatus according to claim 3, wherein the probe can be inserted into a channel of the endoscope.

5. An in-vivo information measurement apparatus according to claim 1,
   wherein the insertion part includes an endoscope and an elongated probe,
   the elongated probe is disposed inside the endoscope, and the endoscope includes, an illumination unit that irradiates the examination site with illumination light;

an objective optical system that forms an image of the examination site; and an imaging unit that acquires the image formed by the objective optical system.

6. An in-vivo information examination apparatus according to claim 5, wherein at least one of the light projection unit and the light receiving unit is disposed inside the field of view of the objective optical system.

7. An in-vivo information measurement apparatus according to claim 5, further comprising:

an image combining device that superimposes the endoscope image obtained by the endoscope and the in-vivo information for the examination site calculated by the in-vivo information calculation unit.

8. An in-vivo information measurement apparatus according to claim 1, wherein the moving mechanism rotates the light projection unit or the light receiving unit about an axis of an endoscope.

9. An in-vivo information measurement apparatus according to claim 1, wherein the moving mechanism translates the light projection unit or the light receiving unit along an axis of an endoscope.

10. An in-vivo information measurement apparatus according to claim 1, further comprising:

an in-vivo information display unit that displays in-vivo information for the examination site, which is calculated by the in-vivo information calculation unit.

11. An in-vivo information measurement apparatus according to claim 10, wherein the insertion part is an endoscope, and the in-vivo information display unit simultaneously displays an image of the surface of the examination site, which is acquired by the endoscope, and the in-vivo information for the examination site.

12. An in-vivo information measurement apparatus according to claim 10, wherein the in-vivo information display unit multi-dimensionally displays the in-vivo information for the examination site.

13. An in-vivo information measurement apparatus according to claim 1, further comprising:

a wavelength selection mechanism, between the light receiving unit and the optical detector, for selectively detecting in the optical detector light of a predetermined wavelength among the return light.

14. An in-vivo information measurement apparatus according to claim 13, wherein the wavelength selection mechanism is formed of a dichroic mirror.

15. An in-vivo information measurement apparatus according to claim 13, wherein the wavelength selection mechanism is formed of a filter that transmits only fluorescence or phosphorescence among the return light.

16. An in-vivo information measurement apparatus according to claim 1, wherein the in-vivo information is the concentration of biological tissue components.

17. An in-vivo information measurement apparatus according to claim 16, wherein the biological tissue components are any of oxygen, hemoglobin, oxygenated hemoglobin, deoxygenated hemoglobin, water, and carbon dioxide.

18. An in-vivo information measurement apparatus according to claim 1, wherein when the light projection unit is aligned with one of the window portions, the light receiving unit is disposed so as to always be aligned with another of the window portions.

* * * * *